United States Patent
Frasier et al.

(10) Patent No.: US 8,057,518 B2
(45) Date of Patent: Nov. 15, 2011

(54) SPANNING CONNECTOR FOR CONNECTING A SPINAL FIXATION ELEMENT AND AN OFFSET BONE ANCHOR

(75) Inventors: William J. Frasier, New Bedford, MA (US); Michael Mahoney, Middletown, RI (US); Nicholas Pavento, Marlboro, MA (US); Christopher L. Ramsay, West Wareham, MA (US); David Greg Anderson, Moorestown, NJ (US)

(73) Assignee: DePuy Spine, Inc., Raynham, MA (US)

( * ) Notice: Subject to any disclaimer, the term of this patent is extended or adjusted under 35 U.S.C. 154(b) by 1110 days.

(21) Appl. No.: 11/897,641

(22) Filed: Aug. 31, 2007

(65) Prior Publication Data

US 2009/0062861 A1     Mar. 5, 2009

(51) Int. Cl.
*A61B 17/70*     (2006.01)

(52) U.S. Cl. ........ 606/267; 606/264; 606/265; 606/266; 606/305

(58) Field of Classification Search .......... 606/264–267, 606/270, 272, 86 A, 306, 308, 320
See application file for complete search history.

(56) References Cited

U.S. PATENT DOCUMENTS

| | | | |
|---|---|---|---|
| 4,653,481 A | 3/1987 | Howland et al. | |
| 5,306,275 A | 4/1994 | Bryan | |
| 5,474,551 A | 12/1995 | Finn et al. | |
| 5,584,834 A | 12/1996 | Errico et al. | |
| 5,609,592 A | 3/1997 | Brumfield et al. | |
| 5,624,441 A | 4/1997 | Sherman et al. | |
| 5,984,922 A | 11/1999 | McKay | |
| 6,261,288 B1 * | 7/2001 | Jackson | 606/250 |
| 6,468,276 B1 | 10/2002 | McKay | |
| 6,562,038 B1 | 5/2003 | Morrison | |
| 6,626,906 B1 | 9/2003 | Young | |
| 6,726,692 B2 | 4/2004 | Bette et al. | |
| 6,770,075 B2 | 8/2004 | Howland | |

(Continued)

FOREIGN PATENT DOCUMENTS

EP     1339337 B1     9/2003

(Continued)

OTHER PUBLICATIONS

Ebara, Sohei et al., "A New System for the Anterior Restoration and Fixation of Thoracic Spinal Deformities Using an Endoscopic Approach," *Spine*, vol. 25(7):876-883 (2000).

*Primary Examiner* — Eduardo C Robert
*Assistant Examiner* — Ellen C. Hammond
(74) *Attorney, Agent, or Firm* — Nelson Mullins Riley & Scarborough LLP

(57) ABSTRACT

A spanning connector for connecting an offset bone anchor to a previously inserted spinal fixation element and method of use is provided. The spanning connector includes a first connecting mechanism for connecting the spanning connector to the bone anchor, and a second connecting mechanism for connector the spanning connector to the previously inserted spinal fixation element. The spanning connector also includes a connector body for coupling the first connecting mechanism and the second connecting mechanism. Embodiments of a spanning connector may also reduce a separation distance between the bone anchor and the spinal fixation element. Embodiments of a spanning connector are configured, sized and dimensioned for use in a minimally invasive surgical technique, such as a rod-first spinal surgical technique.

3 Claims, 24 Drawing Sheets

U.S. PATENT DOCUMENTS

| | | | |
|---|---|---|---|
| 6,964,665 B2 | 11/2005 | Thomas et al. | |
| RE39,035 E | 3/2006 | Finn et al. | |
| 7,166,108 B2 | 1/2007 | Mazda et al. | |
| 7,179,261 B2 | 2/2007 | Sicvol et al. | |
| 7,588,593 B2 * | 9/2009 | Aferzon | 606/265 |
| 7,780,706 B2 * | 8/2010 | Marino et al. | 606/264 |
| 2004/0236330 A1 | 11/2004 | Purcell et al. | |
| 2005/0010216 A1 * | 1/2005 | Gradel et al. | 606/61 |
| 2006/0089651 A1 | 4/2006 | Trudeau et al. | |
| 2006/0111730 A1 | 5/2006 | Hay | |
| 2006/0155278 A1 | 7/2006 | Warnick | |
| 2006/0173456 A1 | 8/2006 | Hawkes et al. | |
| 2006/0235389 A1 * | 10/2006 | Albert et al. | 606/61 |
| 2006/0264934 A1 | 11/2006 | Fallin | |
| 2006/0282074 A1 * | 12/2006 | Renaud et al. | 606/61 |
| 2010/0057140 A1 * | 3/2010 | Zucherman et al. | 606/308 |
| 2010/0198260 A1 * | 8/2010 | Gabelberger et al. | 606/264 |
| 2010/0298890 A1 * | 11/2010 | Marino | 606/305 |

FOREIGN PATENT DOCUMENTS

| | | |
|---|---|---|
| EP | 1405606 A2 | 4/2004 |
| WO | WO-98/49961 A1 | 11/1998 |
| WO | WO-2004/080318 A1 | 9/2004 |
| WO | WO-2006/023514 A1 | 3/2006 |
| WO | WO-2006/047742 A2 | 5/2006 |
| WO | WO-2006/081375 A2 | 8/2006 |

* cited by examiner

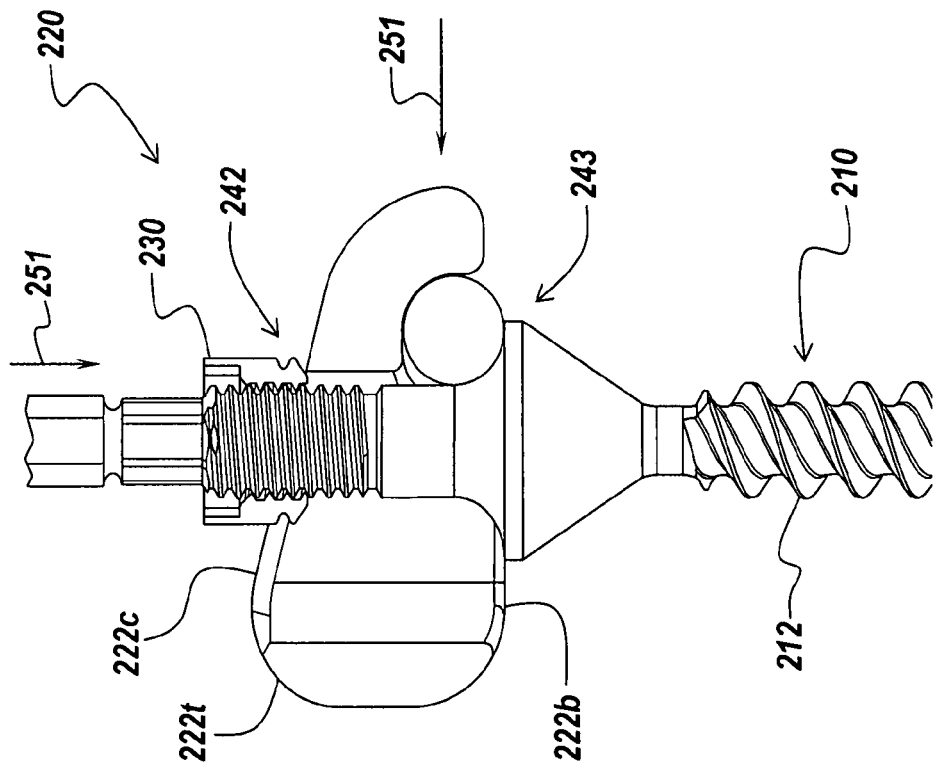
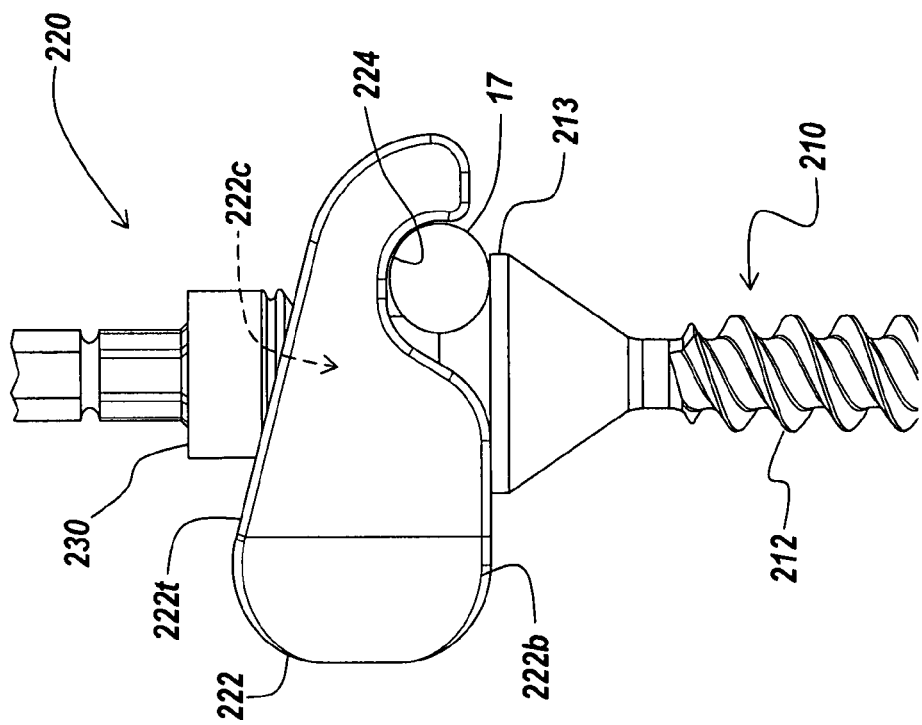
Fig. 9B
Fig. 9A

SPANNING CONNECTOR FOR CONNECTING A SPINAL FIXATION ELEMENT AND AN OFFSET BONE ANCHOR

FIELD OF INTEREST

The present invention relates to connector devices and methods for use during orthopedic surgery. More particularly, the present invention relates to connectors for connecting spinal fixation elements and offset bone anchors.

BACKGROUND

For a number of known reasons, spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation elements can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation elements can be anchored to specific portions of the vertebrae. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, or similar type of fastening mechanism is used to lock the fixation element, e.g. a rod, into the rod-receiving head of the pedicle screw. In use, the shank portion of each screw is threaded into a vertebra, and once properly positioned, a rod is seated through the rod-receiving member of each screw and the rod is locked in place by tightening a cap or other fastener mechanism to securely interconnect each screw and the fixation rod.

Recently, the trend in spinal surgery has been moving toward providing minimally invasive elements and methods for implanting spinal fixation devices. For example, one such method, a rod-first method, includes inserting a spinal rod through a first incision and positioning the spinal rod along a patient's spinal column adjacent to one or more vertebra. After the spinal rod is inserted, a first bone anchor is inserted through the first incision or through a separate incision, and then additional bone anchors are inserted each through a separate incision along the spinal rod. After a bone anchor is inserted and anchored in bone it is coupled to the spinal rod. A rod-first method is a minimally invasive technique in which the bone anchors are inserted after the rod and adjacent to the rod, as opposed to a conventional surgical technique in which the bone anchors are inserted first then the rod is placed in rod-receiving elements lying over the heads of the bone anchors.

Unfortunately, one or more bone anchors may not be inserted immediately adjacent to the spinal rod. Additionally, in many instances one or more vertebrae are out of alignment such that the one or more vertebrae and the inserted bone anchor are not immediately adjacent to the inserted spinal rod. In percutaneous or minimally invasive procedures, it is more difficult to adjust a spinal rod using a technique such as bending to make contact between the spinal rod and the bone anchors. It is also it is more difficult to move such displaced vertebrae so that the vertebrae may be coupled to the spinal rod. Thus, there is a need for a spanning connector for connecting a previously inserted spinal fixation element, such as a spinal rod, with an offset bone anchor in a minimally invasive surgical procedure. There is also a need for a spanning connector suitable for use in a minimally invasive surgical procedure that can approximate, e.g. move, a displaced vertebra toward the spinal fixation element.

SUMMARY

In accordance with a first aspect, a spanning connector is provided for connecting a spinal fixation element (SFE) to an offset bone anchor. The spanning connector includes a first connecting mechanism for coupling the spanning connector to the bone anchor and a second connecting mechanism for coupling the spanning connector to the previously inserted spinal fixation element. The spanning connector also includes a connector body for coupling the first connecting mechanism with the second connecting mechanism.

In certain embodiments, the spanning connector may also include an approximation mechanism configured to approximate, e.g. move, a bone anchor to reduce a separation distance between the bone anchor and the SFE. The second connecting mechanism may be configured to engage the SFE either from a side or from above. The first connecting mechanism may be configured to connect the spanning connector to a shaft of the bone anchor. The first connecting mechanism may be configured to connect the spanning connector to a head of the bone anchor.

In certain embodiments, the connector body of the spanning connector may have a telescoping mechanism configured to adjust to a separation distance between the offset bone anchor and the SFE by changing a length of the spanning connector. The connector body may be configured to rotate about the head of the bone anchor from an insertion configuration to an engagement configuration.

In other embodiments, the second connecting mechanism may include a collar slidably coupled with the SFE. An extender may be coupled with the collar. The connector body may include a receiver for receiving the extender and a securing element for securing the extender to the connector body.

In another embodiment, the spanning connector may include a gear drive for extending and retracting a connector arm. An SFE engager for engaging the SFE is attached to an end of the connector arm. The gear drive may approximate an offset bone anchor by retracting the connector arm after the SFE is coupled with the SFE engager.

Another exemplary embodiment includes a method of using a spanning connector to couple an offset bone anchor to a previously inserted spinal fixation element. The method includes providing a spanning connector having a first connecting mechanism, a second connecting mechanism and a connector body. The first connecting mechanism is configured to couple the bone anchor with the spanning connector. The second connecting mechanism is configured to couple the SFE with the spanning connector. The connector body is configured to couple the first connecting mechanism and the second connecting mechanism. The method also includes coupling the connector body to the bone anchor using the first connecting mechanism and inserting the connector body and the bone anchor into a patient. The method further includes coupling the spanning connector to the SFE using the second connecting mechanism.

BRIEF DESCRIPTION OF THE FIGURES

These and other features and advantages of the devices and methods disclosed herein will be more fully understood by reference to the following detailed description in conjunction with the attached drawings in which like reference numerals refer to like elements through the different views. The drawings illustrate principles of the instruments and methods disclosed herein and, although not to scale, show relative dimensions.

FIG. 9A illustrates a side view of a clamp-type spanning connector including an approximation mechanism, according to aspects of an exemplary embodiment;

FIG. 9B illustrates a cross-sectional side view of the spanning connector depicted in FIG. 9A;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Exemplary embodiments described herein concern spanning connectors for connecting spinal fixation elements to offset bone anchors (such as a pedicle bone screws or anchor bolts) and methods of use. Exemplary embodiments of a spanning connector are particularly suited for use in a rod-first spinal surgical technique in which the bone anchor inserted into a patient vertebra may be separated from the SFE by a distance. An exemplary embodiment of a spanning connector couples the previously inserted spinal fixation element with an offset bone anchor. Some exemplary embodiments of a spanning connector also approximate a bone anchor by reducing the distance between the SFE and the bone anchor. Exemplary embodiments of a spanning connector are sized and dimensioned for insertion through a minimally invasive surgical access port, such as a cannula. Additionally, exemplary embodiments of a spanning connector are configured for use in a rod-first surgical technique in which an SFE is inserted and positioned in a patient before insertion of bone anchors, and in which the bone anchors are positioned adjacent to an SFE and not beneath the SFE.

As described herein, an offset bone anchor is a bone anchor that has been inserted into a patient vertebra and anchored in bone, and is separated by a distance from an SFE inserted into position in the patient before the insertion of the bone anchor. Ideally, exemplary embodiments of a spanning connector can couple an SFE and a bone anchor separated by a distance of at least about 2 mm. Some embodiments may couple an SFE and a bone anchor separated by a distance of about 10 mm, for example in cases of spinal deformities.

Figure 1A:
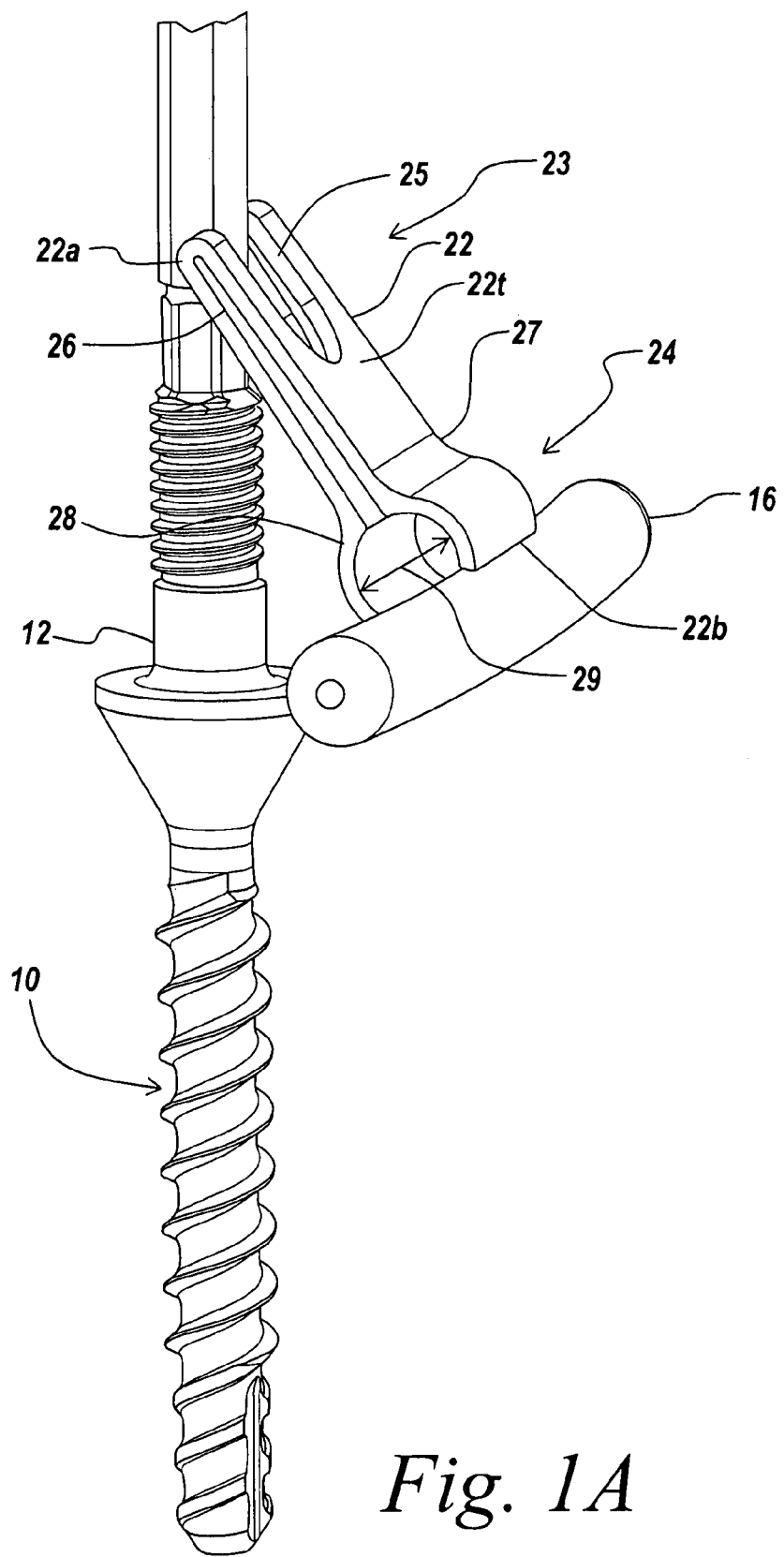
FIG. 1A illustrates an exemplary embodiment of a spanning connector.
Figure 1B:
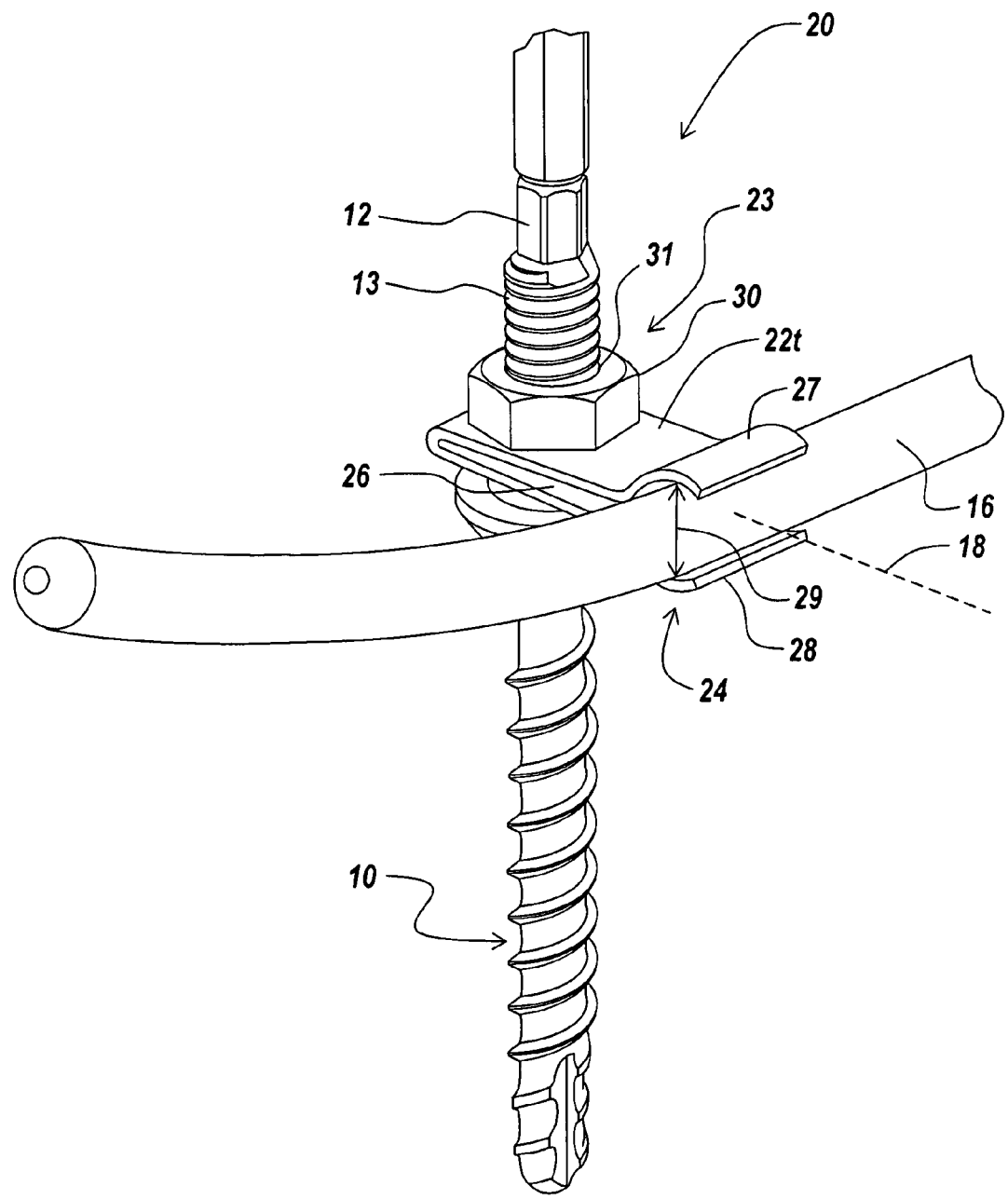
FIG. 1B illustrates the spanning connector of FIG. 1A in use connecting a bone anchor and an SFE.

FIGS. 1A and 1B illustrate an exemplary embodiment of a spanning connector 20 for connecting a previously inserted spinal fixation element 16 to an offset bone anchor 10. The spanning connector 20 includes a first connecting mechanism 23 for coupling the spanning connector 20 to the bone anchor 10 and a second connecting mechanism 24 for coupling the spanning connector 20 to the SFE 16. The spanning connector 20 also includes a connector body 22 for coupling the first connecting mechanism 23 with the second connecting mechanism 24.

The bone anchor 10 may have been inserted by any appropriate method, ideally a minimally invasive method, including using a cannula, k-wire, etc. Techniques and instruments for minimally invasive insertion of a bone anchor and a connecting element are discussed in detail in the related applications: application DUQ-034 entitled "Minimally Invasive Guide System," filed on Aug. 31, 2007, and DUQ-037 entitled "Method and System for Securing a Rod to a Bone Anchor with a Connector," filed on Aug. 31, 2007.

According to aspects of an exemplary embodiment, the first connecting mechanism 23 may include an opening 25 in a first end 22a of the connector body 22 for receiving a shaft 12 of the bone anchor 10. The opening 24 may be a slot in the connector body 22 as depicted, or a circular or elongate hole through the connector body 22. The first connecting mechanism 23 may also include a securing element 30 having a hole 31 for passing the shaft 12 of the bone anchor 10 through. The securing element 30 is configured to exert a compressive force against a top side 22t of the connector body 22. The securing element 30 may be a nut configured to engage threads 13 on the shaft 12 of the bone anchor 10 as depicted.

According to further aspects of the exemplary embodiment, the second connecting mechanism 24 may include a slot 26 extending from a second end 22b of the connector body 22 and forming a top arm 27 and a bottom arm 28. The top arm 27 and the bottom arm 28 are joined at the first end 22a of the connector body 22. A receiving slot gap 29 between the top arm 27 and the bottom arm 28 is configured to receive the SFE 16. The compressive force exerted by the securing element 30 against the top side 22t of the connector body 22 causes a width of the receiving slot gap 29 to decrease, securing the SFE 16 to the connector body 22. The securing element 30 secures the first end 22a of the connector body 22 to the bone anchor 10 and secures the SFE 16 to the second end 22b of the connector body 22.

In this exemplary embodiment, the spanning connector 20 is configured for side engagement with the SFE 16, where side engagement is displacement of the SFE 16 with respect to the bone anchor 10 substantially along an engagement axis 18 perpendicular to both the shaft 12 of the bone anchor 10 and the SFE 16. Although the spanning connector 20 is configured to allow side engagement with the SFE 16, it can also engage the SFE 16 from a substantially vertical direction. The spanning connector 20 may be sized, dimensioned and configured for insertion thorough a minimally invasive surgical port. As illustrated in FIG. 1A, the spanning connector 20 may be inserted into the patient at an angle to the shaft 12 of the bone anchor 10 with the first end 22a of the connector body 22 leading the second end 22b of the connector body 22 to reduce an insertion profile of the spanning connector 20.

Figure 2A:
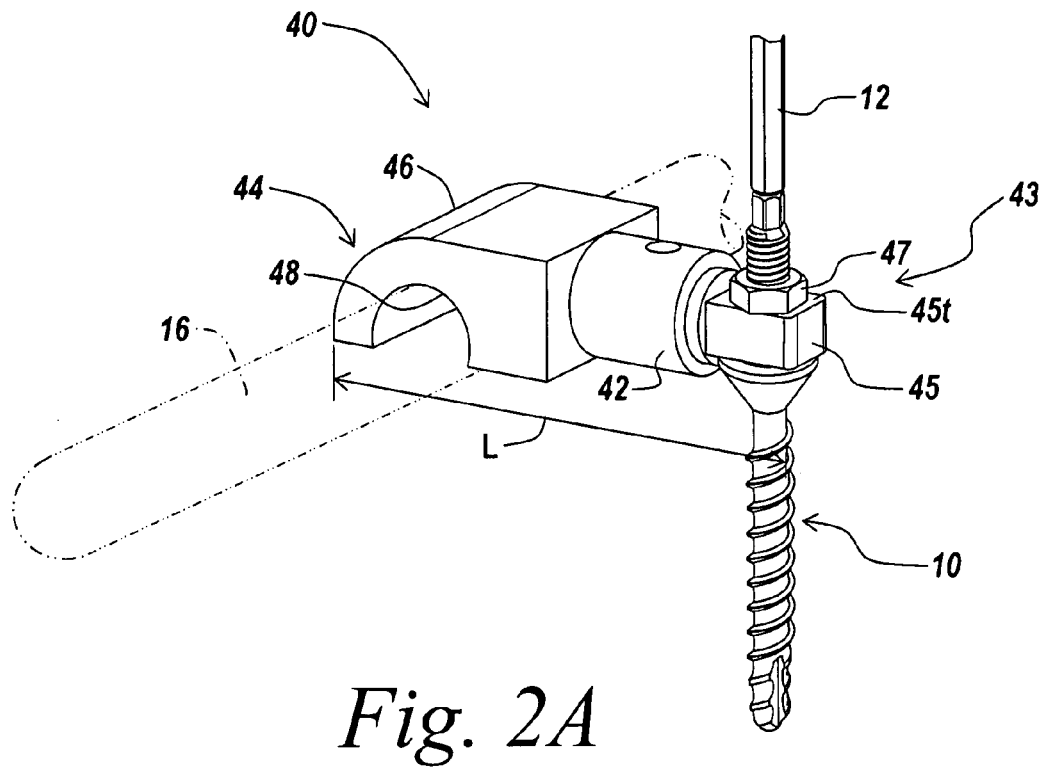
FIG. 2A illustrates an exemplary embodiment of a telescoping spanning connector, according to aspects of an exemplary embodiment.
Figure 2B:
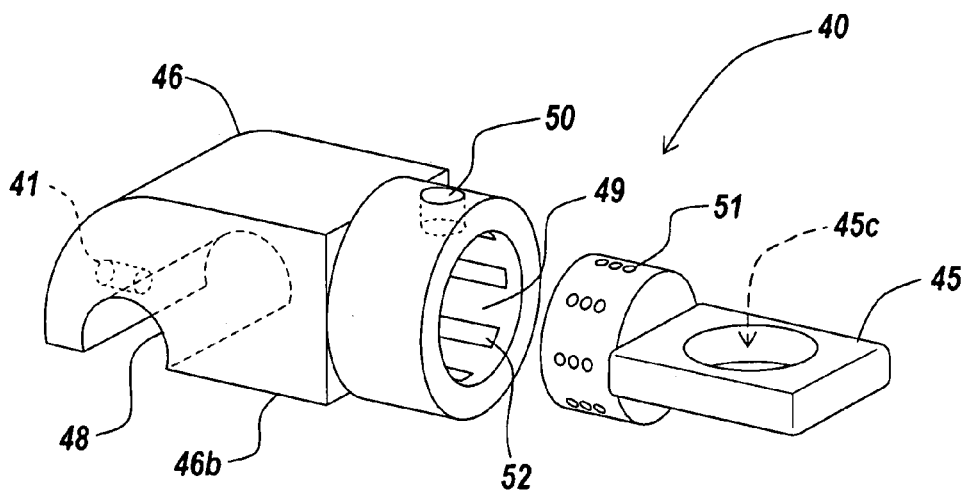
FIG. 2B illustrates an exploded view of the telescoping spanning connector depicted in FIG. 2A.

FIGS. 2A and 2B illustrate an exemplary embodiment of a spanning connector 40 including a telescoping mechanism to adjust to a distance between the SFE 16 and a bone anchor, such as the bone anchor 10. The spanning connector 40 includes a connector body 42, a first connecting mechanism 43 for coupling the spanning connector 40 to the bone anchor 10 and a second connecting mechanism 44 for coupling the spanning connector 40 to the SFE 16. According to aspects of the exemplary embodiment, the connector body 42 may include a first piece 45, and a second piece 46 configured to slidably couple with the first piece 45. The slidable coupling between the first piece 45 an the second piece 46 allow the spanning connector 40 to change its length L forming the telescoping mechanism. The first connecting mechanism 43 may include a channel 45c disposed in the first piece 45 for passing a shaft 12 of the bone anchor 10 therethrough. The second connecting mechanism 44 may include a elongate recess 48 disposed in the second piece 46 and configured to receive and partially encircle the SFE 16.

According to further aspects of an exemplary embodiment, the connector body 22 may also include a cavity 49 formed between the first piece 45 and the second piece 46 as illustrated by the exploded view of the spanning connector 40 depicted in FIG. 2B. The connector body 42 may also include an injection lumen 50 that connects the cavity 49 to space external to the connector body 42. Non-solid hardenable media may be injected into the cavity 49 through the injection lumen 50 when the connector body 22 is in a shortened state with the cavity 49 at a minimum size. The non-solid hardenable media fills the cavity 49 and exerts pressure on the first piece 45 and the second piece 46 causing the first piece 45 and the second piece 46 to slide away from each other lengthening the spanning connector 40 until it spans the distance between the SFE 16 and the bone anchor 10. After the non-solid hardenable media hardens, the first piece 45 and the second piece 46 are locked in position relative to each other. The first piece 45 may include external surface recesses 51 located where the first piece 45 slidably couples with the second piece 46, and the second piece 46 may include internal surface recesses 52 where the second piece 46 slidably couples with the first piece 45. The external surface recesses 51 and internal surface recesses 52 allow the non-solid hardenable media to enter the slidable coupling for a more secure attachment between the first piece 45 and the second piece 46.

According to other aspects of an exemplary embodiment, the elongate recess 48 may be formed in a bottom side 46b of the second piece 46. This placement of the elongate recess 48 allows the second piece 46 to engage the SFE 16 from above. The spanning connector 40 may also include a first securing element 47 configured to exert a compressive force against a top side 45t of the first piece 45, securing the first piece 45 to the bone anchor 10. The spanning connector 40 may also include a second securing element 41 for securing the SFE 16 in the elongate recess 48 of the second piece 46.

Figure 3A:
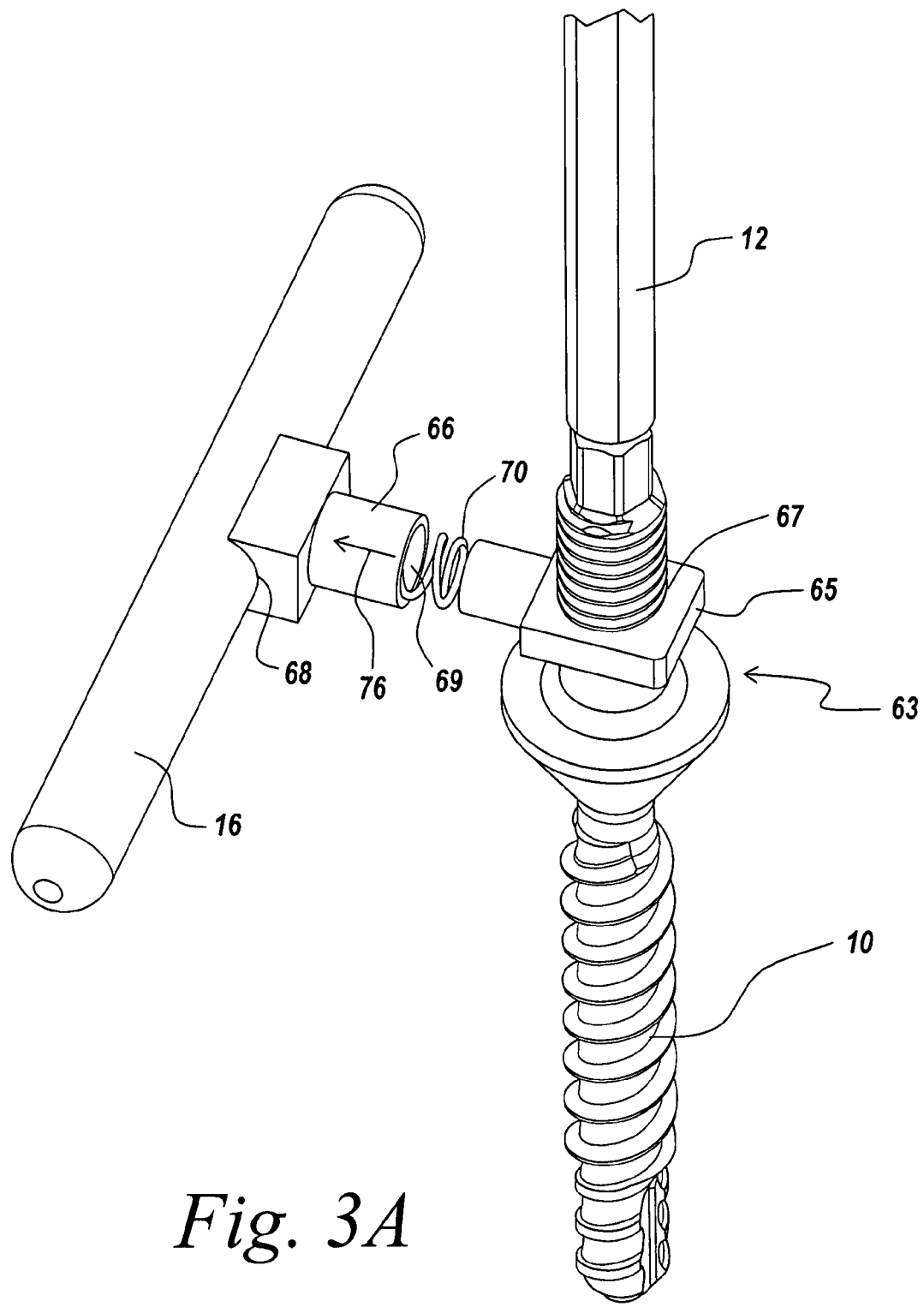
FIG. 3A illustrates an exemplary embodiment of a spring-loaded telescoping spanning connector.
Figure 3B:
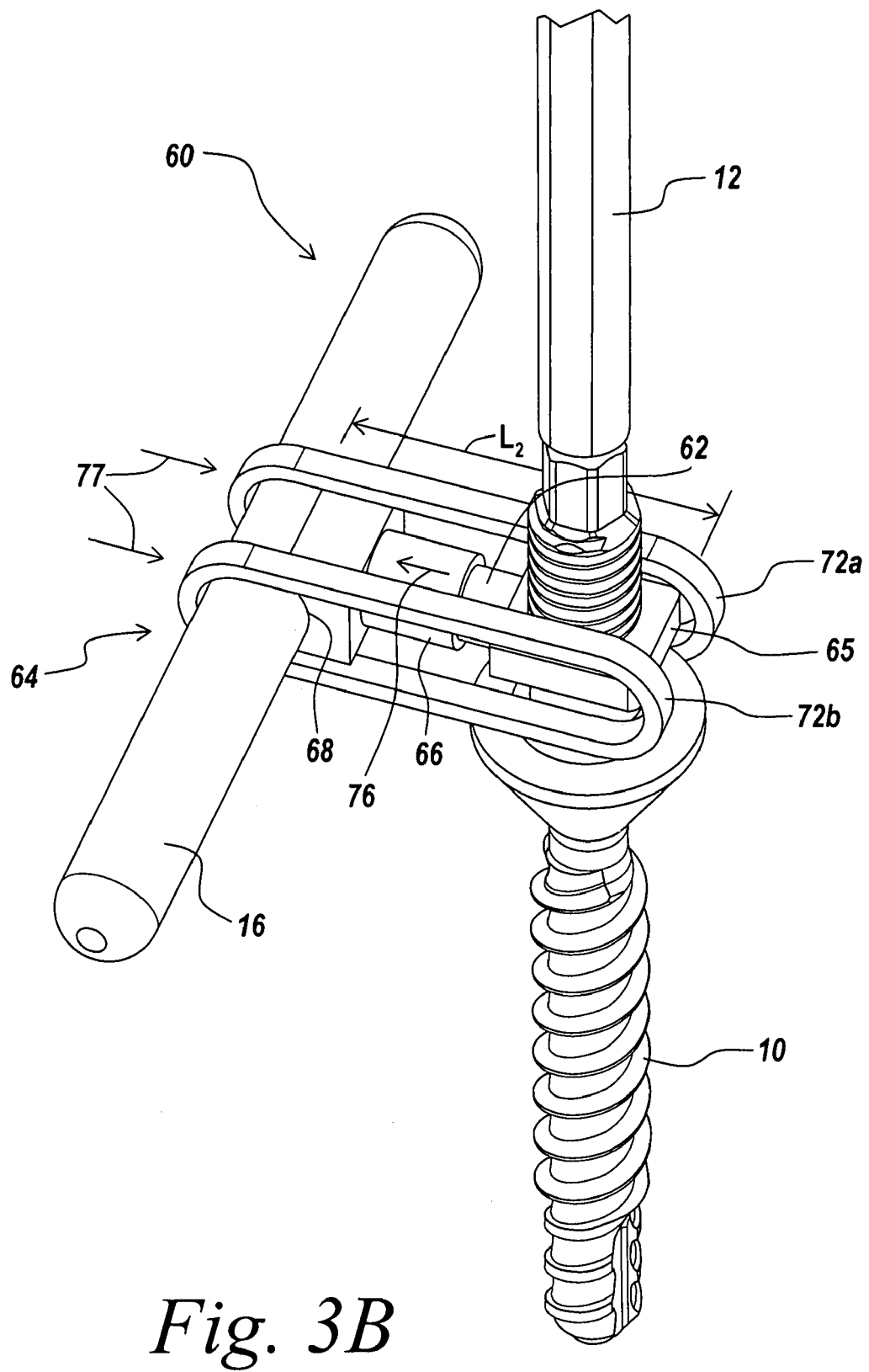
FIG. 3B illustrates the telescoping spanning connector depicted in FIG. 3A after flexible elongate elements have been secured.

FIGS. 3A and 3B illustrate another exemplary embodiment of a spanning connector 60 that includes a telescoping mechanism for connecting a bone anchor, such as the bone anchor 10, to the SFE 16. The spanning connector 60 includes a connector body 62, a first connecting mechanism 63 for connecting the spanning connector 60 to the previously inserted bone anchor 10 and a second connecting mechanism 64 for connecting the spanning connector 60 to the SFE 16.

According to aspects of an exemplary embodiment, the connector body 62 may include a first piece 65, and a second piece 66 configured to slidably couple with the first piece 65 to change a length $L_2$ of the spanning connector 60 forming the telescoping mechanism. The first connecting mechanism 63 may include a channel 67 disposed in the first piece 65 of the connector body 62 for passing a shaft 12 of the bone anchor 10 therethrough. The second connecting mechanism 64 may include a elongate recess 68 disposed in the second piece 66 and configured to receive and partially encircle the SFE 16.

The first piece 65 and the second piece 66 may form a cavity 69. The connector body 62 may also include a spring 70 disposed in the cavity 69. The spring 70 exerts a force on the second piece 66 that biases the second piece 66 outward as indicated by arrow 76. The outward force is transmitted to the SFE 16 through contact with the elongate recess 68. The second securing mechanism 64 may further include a plurality of flexible elongate elements, such as cables 72a, 72b.

Each cable 72a, 72b is configured to encircle the SFE 16 and couple the SFE 16 with the first piece 65. Tension in each cable 72a, 72b exerts an inward force on the SFE 16 directed toward the first piece 65 as indicated by arrows 77. The inward forces 77 from cable tension are balanced by the outward force (arrow 76) from the compressed spring 70 securing the SFE 16 in the elongate recess 68 of the spanning connector 60. The outward biasing force 76 from the spring causes the spanning connector 60 to lengthen to adjust to a displacement between the bone anchor 10 and the SFE 16.

The elongate body 62 of the spanning connector 60 may be positioned on the previously inserted bone anchor 10 and put in contact with the SFE 16 before the cables 72a and 72b are positioned and secured, as depicted in FIG. 3A. After the spanning connector 60 is positioned and the SFE 16 is seated in the elongate recess 68 of the second piece 66, the cables 72a and 72b are tightly wrapped around the SFE 16 and the first piece 65 and secured, as depicted in FIG. 3B. The flexible elongate elements, such as cables 72a, 72b, may be glued, tied, crimped, etc. to form bands around the SFE 16 and the first piece 65.

Figure 4A:
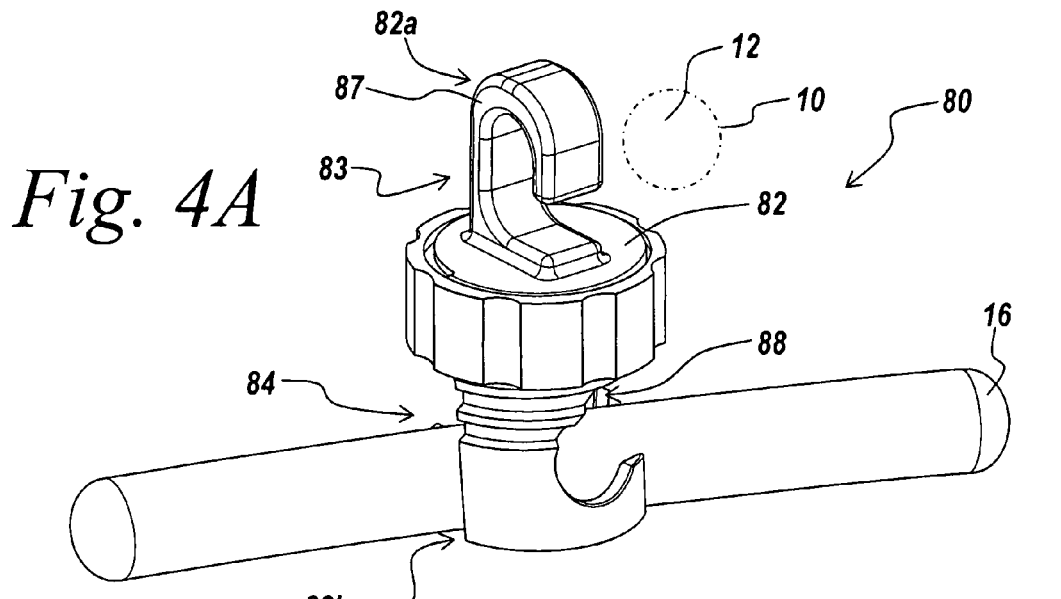
FIG. 4A illustrates an exemplary embodiment of a spanning connector with twisting spinal fixation element engagement.

FIG. 4A illustrates another exemplary embodiment of a spanning connector 80. The spanning connector 80 engages and secures the SFE 16 with a twisting motion. The spanning connector 80 includes a first connecting mechanism 83 for coupling the spanning connector 80 with the bone anchor 10, and a second connecting mechanism 84 for coupling the spanning connector with the previously inserted spinal fixation element 16. The spanning connector 80 also includes a connector body 82 for coupling the first connecting mechanism 83 and the second connecting mechanism 84.

Figure 4B:
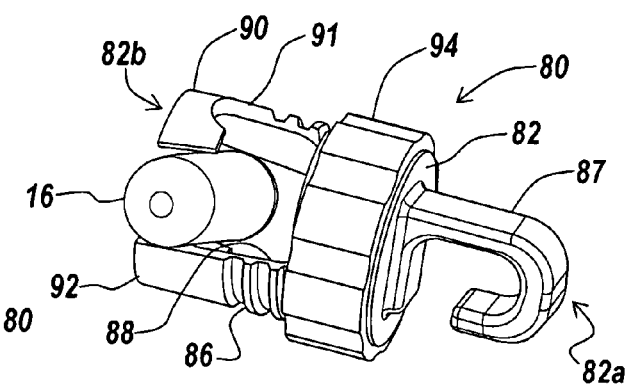
FIG. 4B illustrates the spanning connector receiving the SFE.
Figure 4C:
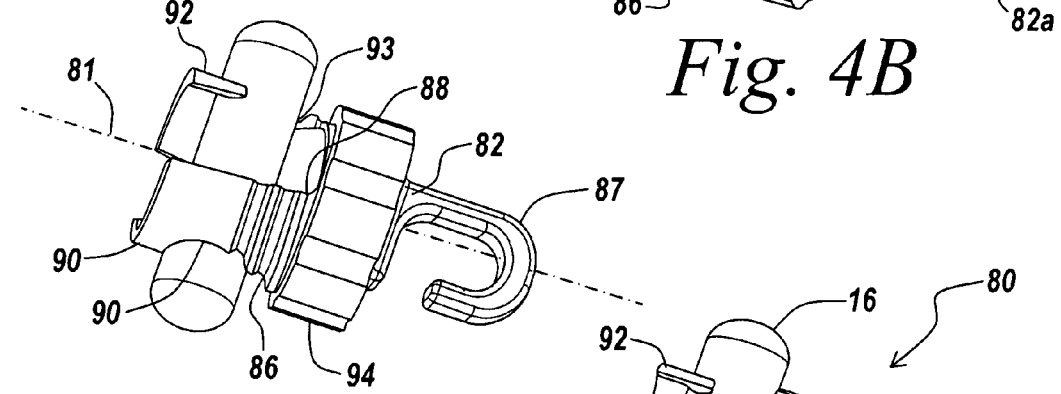
FIG. 4C illustrates the spanning connector after the spanning connector is rotated relative to the SFE.
Figure 4D:
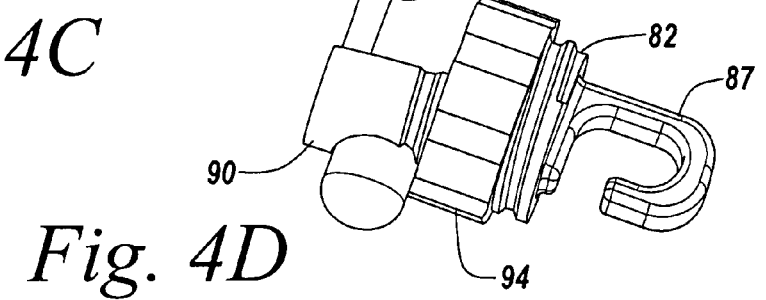
FIG. 4D illustrates the spanning connector after the SFE is engaged and secured.

According to aspects of an exemplary embodiment, the first connecting mechanism 83 may include a hook projection 87 disposed at a first end 82a of the connector body 82. The hook projection 87 is configured to engage the shaft 12 of the bone anchor 10. The hook projection 87 may substantially lie in a plane. The second connecting mechanism 84 may include a main slot 88 extending from a second end 82b of the connector body 82 and oriented perpendicular to the plane of the hook projection 87. The main slot 88 is configured to receive the SFE 16 as depicted in FIG. 4B. The main slot 88 defines a first arm 90 and a second arm 92 disposed at the second end 82b of the connector body 82. The first arm 90 and the second arm 92 each have a receiving slot 91, 93 configured to receive the SFE 16 from the main slot 88 when the connector body 82 is rotated about a central axis 81 of the connector body 82 with respect to the SFE 16, as depicted in FIG. 4C. The second connecting mechanism 84 may also include a threaded locking element 94 configured to engage external threads 86 of the connector body 82. The locking element 94 may be rotated with respect to the connector body 82 to move the locking element 94 toward the second end 82b of the connector body 82. The locking element 94 is configured to block a portion of the main slot 88 trapping the SFE 16 in the receiving slot 91 of the first arm 90 and the receiving slot 93 of the second arm 92, as depicted in FIG. 4D.

The spanning connector 80 is coupled with the SFE 16 before the hook projection 87 is coupled with a shaft 12 of the bone anchor 10. Because the spanning connector 80 is not initially coupled with the shaft 12 of the bone anchor 10, the spanning connector 80 is free to engage the SFE 16 from many different directions. When using the spanning connector 80 in a rod-first surgical technique, engagement of the SFE 16 from a side and engagement of the SFE 16 from above are particularly useful engagement geometries.

Figure 5A:
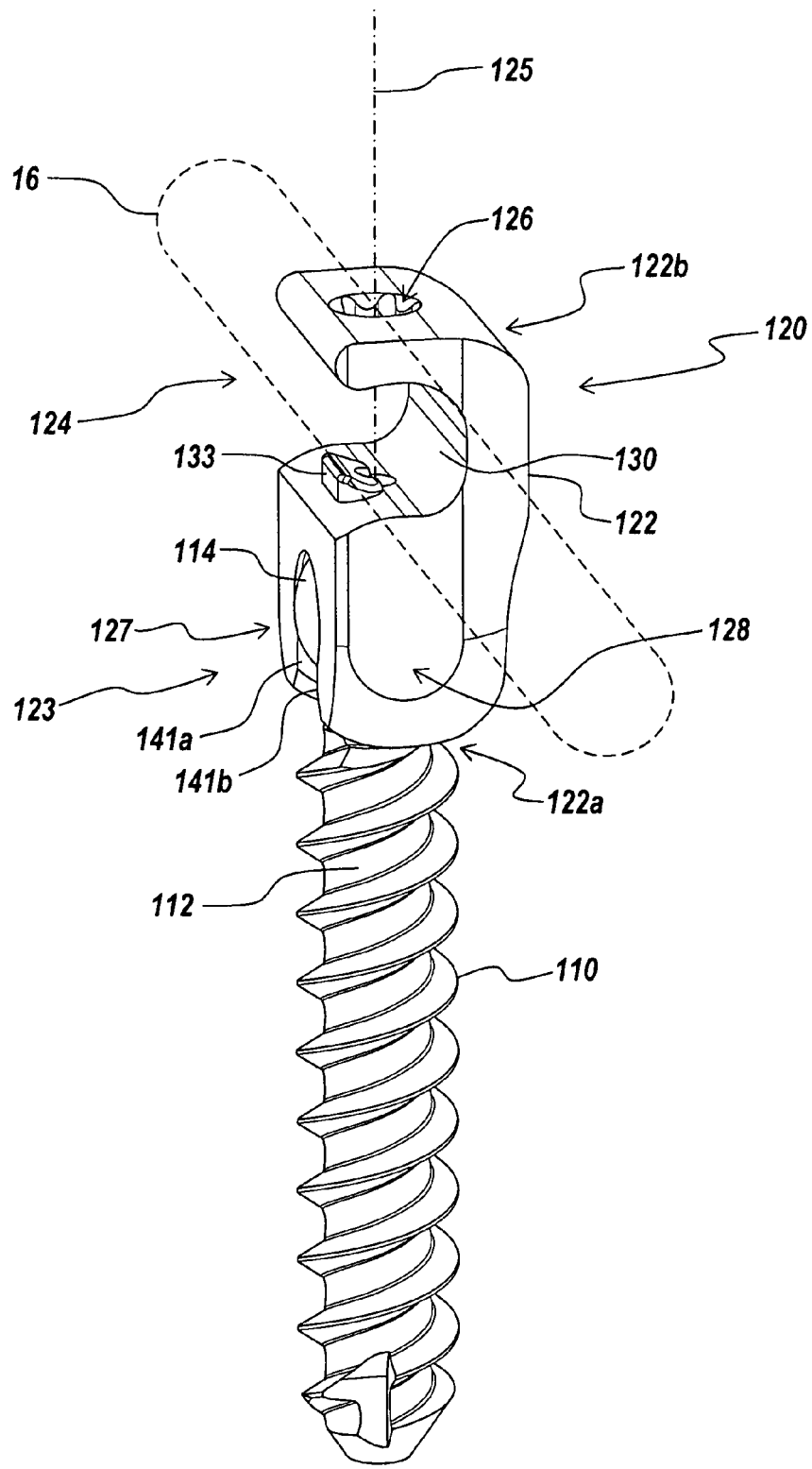
FIG. 5A illustrates an exemplary embodiment of a spanning connector that couples with a head of the bone anchor and rotates from an insertion configuration to an engagement configuration.
Figure 5B:
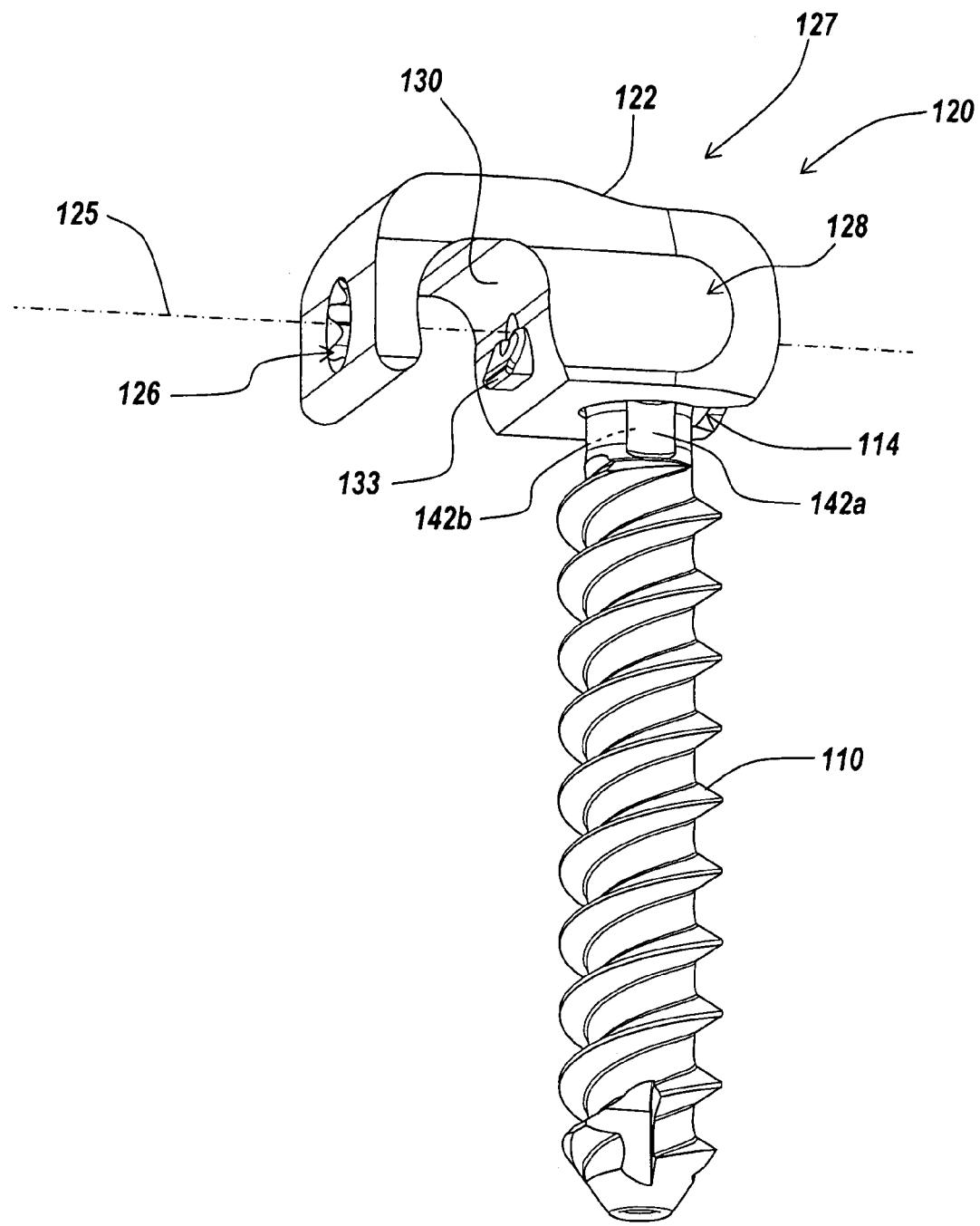
FIG. 5B illustrates the spanning connector depicted in FIG. 5A in an engagement configuration.

FIGS. 5A and 5B illustrate another exemplary embodiment of a spanning connector 120. The spanning connector 120 couples directly with a head of a bone anchor, such as a head 114 of a bone anchor 110. The spanning connector 120 includes a first connecting mechanism 123 for coupling the spanning connector 120 with a bone anchor 110 and a second connecting mechanism 124 for coupling the spanning connector 120 with the SFE 16. The spanning connector 120 also includes a connector body 122 for coupling the first connecting mechanism 123 and the second connecting mechanism 124.

According to aspects of an exemplary embodiment, the connector body 122 may have an access channel 126 extending through the connector body 122, and through the bone anchor 110, parallel to a central axis 125 of the connector body 122. The access channel 126 allows passage of a k-wire through the bone anchor 110 when the connector body 122 is in an insertion configuration with the central axis 125 of the connector body 122 parallel to a shaft 112 of the bone anchor 110, as depicted in FIG. 5A. The first connecting mechanism 123 can include a rotatable coupling 128 disposed at a first end 122a of the connector body 122 for rotatably coupling the first end 122a of the connector body 122 to the bone anchor head 114. The rotatable coupling 128 is configured to permit the connector body 122 to rotate between the insertion configured (depicted in FIG. 5A) and an engagement configuration with the central axis 125 of the connector body 122 perpendicular to a shaft 112 of the bone anchor 110, as depicted in FIG. 5B. The second connecting mechanism 124 can include an engaging elongate recess 130 formed in the connector body 122 and configured to engage the SFE 16 from above when the connector body 122 is in the engagement configuration. The engaging elongate recess 130 is also configured to partially encircle the engaged spinal fixation element 16.

Figure 5C:
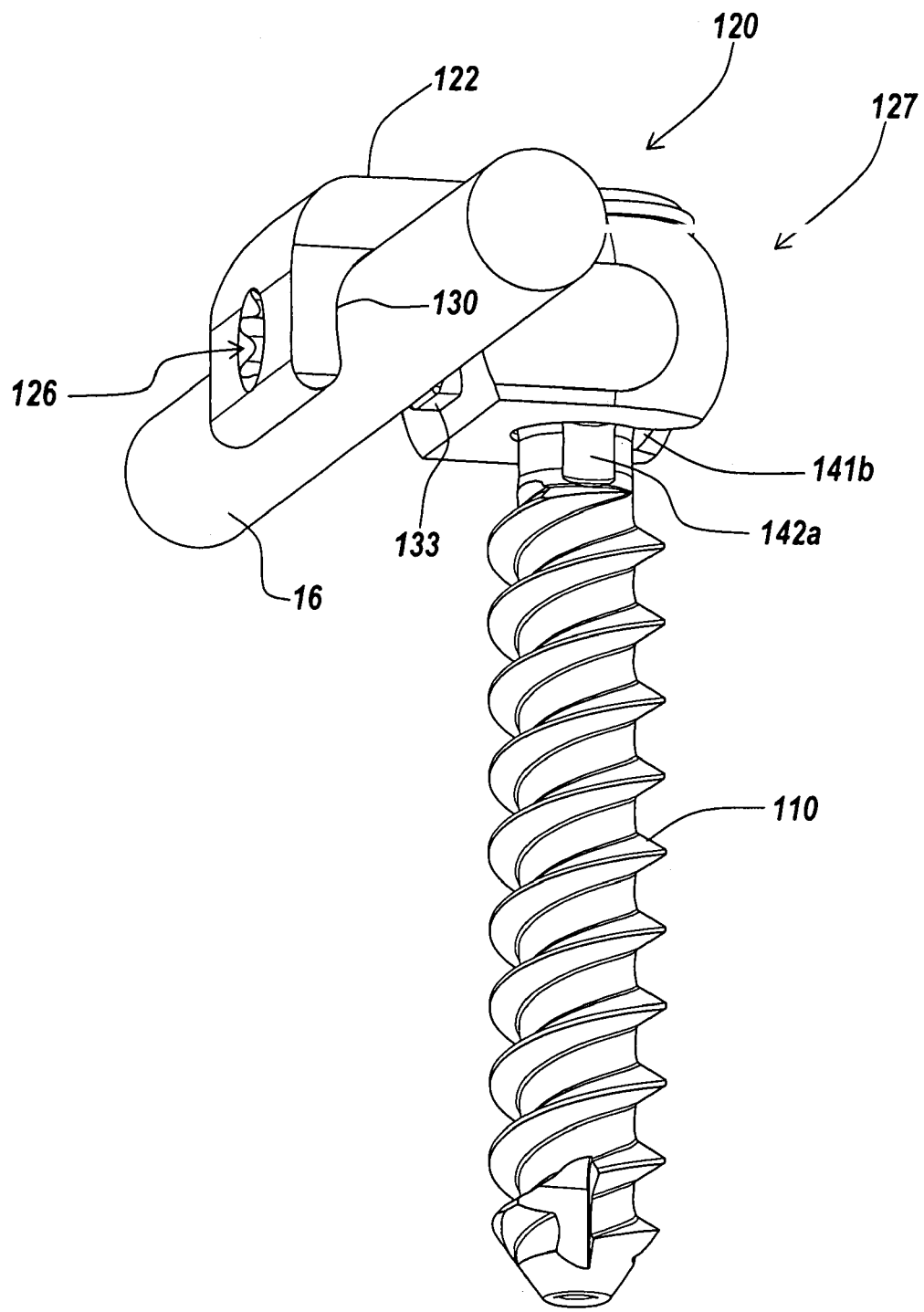
FIG. 5C illustrates the spanning connector depicted in FIG. 5A in use coupled with an SFE.
Figure 5D:
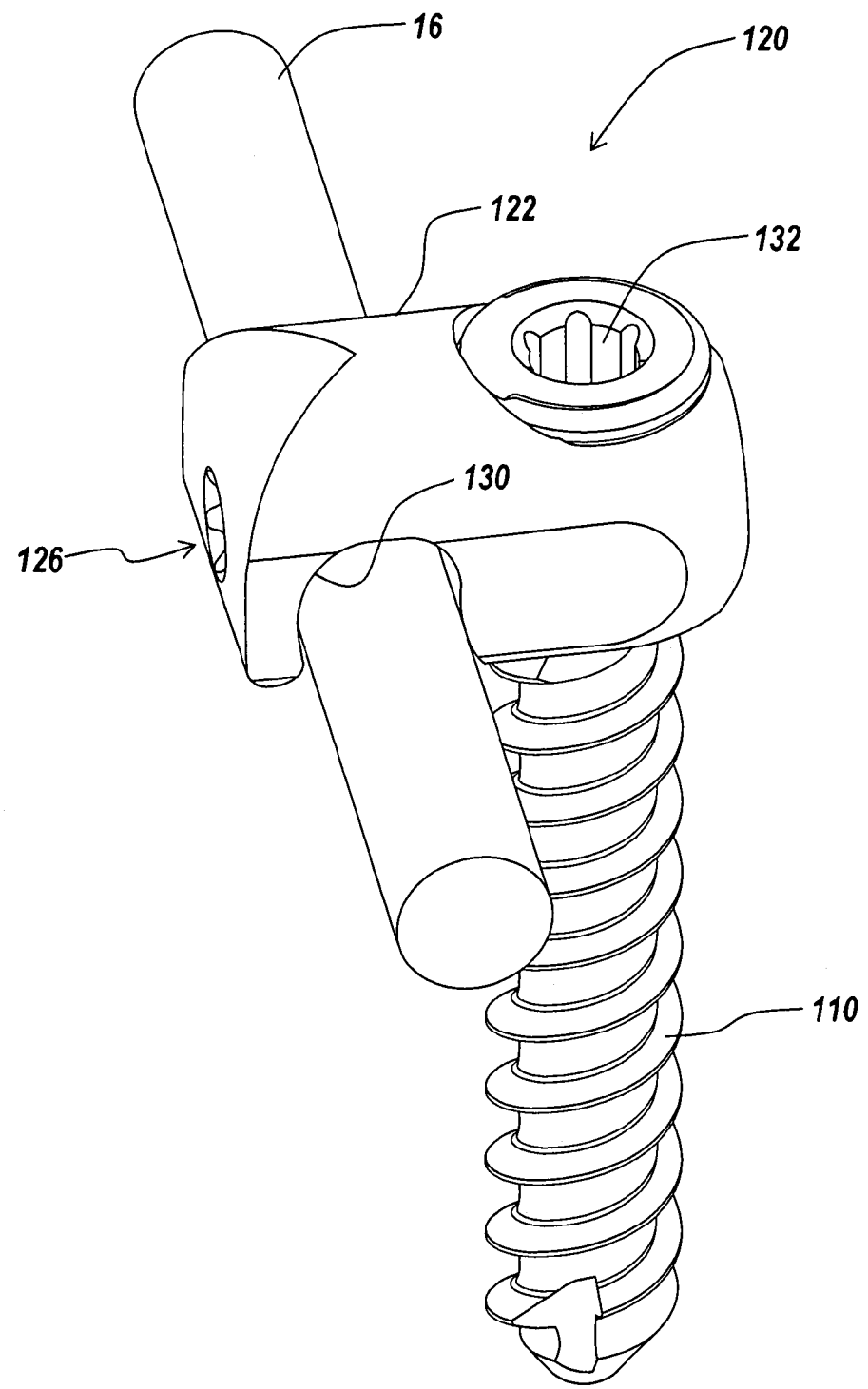
FIG. 5D illustrates another perspective view of the spanning connector in use coupled with an SFE.
Figure 5E:
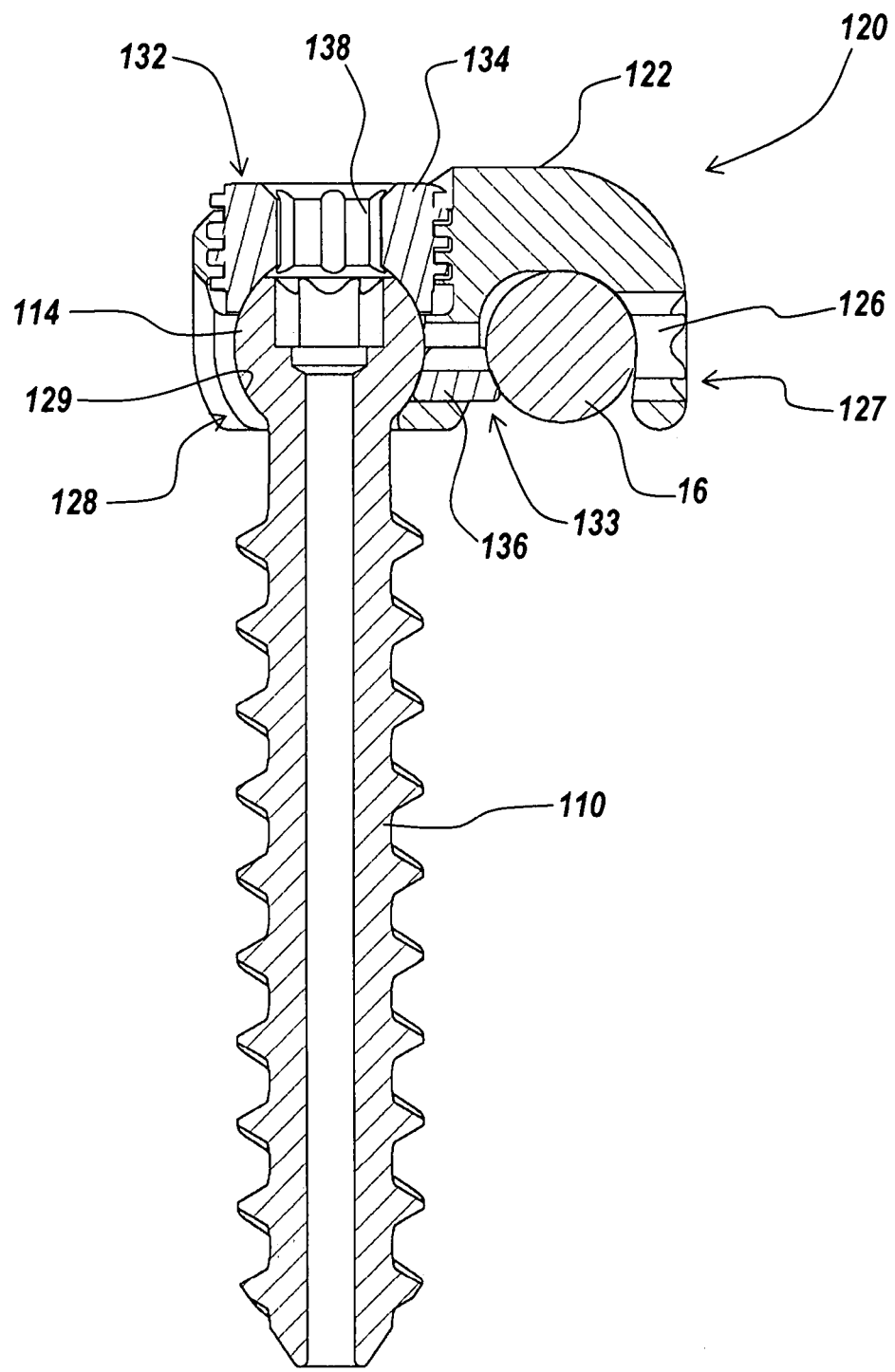
FIG. 5E illustrates a cross-sectional view of the spanning connector depicted in FIG. 5A.

According to other aspects of an exemplary embodiment, the connector body 122 may also include an SFE 133 for securing the SFE in the receiving elongate recess 130. The connector body 122 may also include a screw lock 132 for locking a position of the connector body 122 relative to the bone anchor 110, as illustrated in FIGS. 5C and 5D which present different perspective views of the spanning connector 120 coupled with the SFE 16. FIG. 5E, a cross-sectional view of the spanning connector 120, illustrates details of the access channel 126, the rotatable coupling 128, the SFE lock 133 and the screw lock 132.

The rotatable coupling 128 may be a substantially spherically shaped socket 129 configured to rotatably seat a substantially spherically shaped bone anchor head 114. The screw lock 132 may be a threaded element 134 configured to exert a downward force on the bone anchor head 114 when tightened. The SFE lock 133 may be a sliding element 136 configured to be pushed toward the second end 122b of the spanning connector 122 when the bone anchor head 114 feels a downward force from the threaded element 134. The screw lock 132 and the SFE lock 133 may be controlled by different elements, or the screw lock 132 and the SFE lock 133 may be controlled by the same element, such as a set screw 138, as depicted in FIG. 5E.

As illustrated in FIG. 5C, an exemplary spanning connector 120 may also include a drive mechanism 127 that allows the bone anchor 110 to be driven by the bone anchor head 114 when the connector body 122 is in an insertion configuration (as depicted in FIG. 5A), but does not allow the bone anchor 100 to be driven by the bone anchor head 114 when the connector body 122 is in an engagement configuration (as depicted in FIGS. 5B, 5C and 5D). Connector body 122 may have flat surfaces 141a, 141b in an internal cavity that contact the bone anchor head 114. The bone anchor head 114 may have corresponding flat sides 142a, 142b that allows the bone anchor 110 to be driven by the bone anchor head 114 when the connector body 122 is in position depicted in FIG. 5A, but does not allow the bone anchor 110 to be driven by the bone anchor head 114 when the connector body is in the position depicted in FIG. 5C. The flat surfaces 141a, 141b, of the internal cavity of the bone anchor head 114 and the flat sides 142a, 142b of the bone anchor head 114 may form the drive mechanism 127.

Figure 6A:
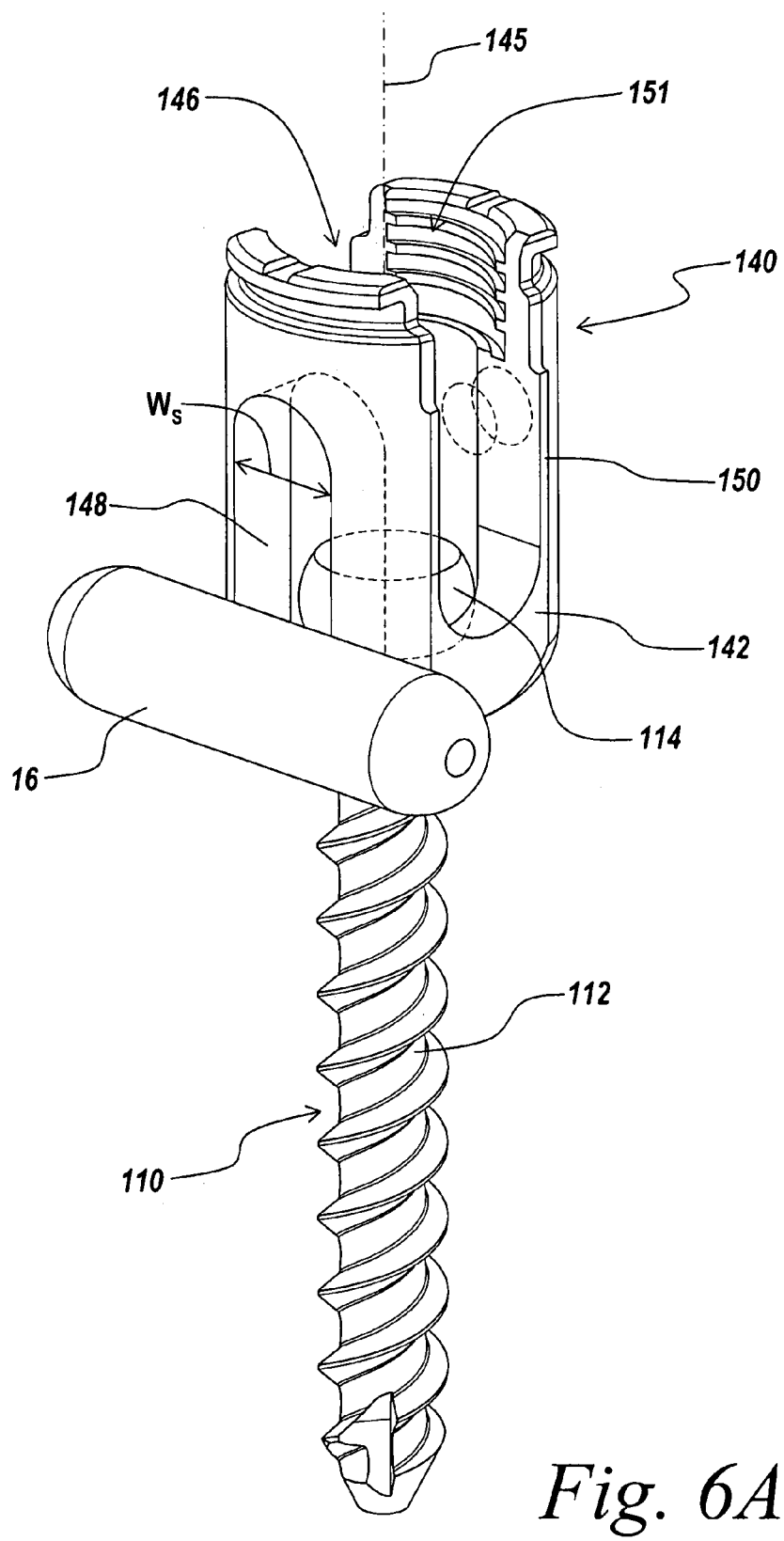
FIG. 6A illustrates an exemplary embodiment of a spanning connector that rotates and slides to engage an SFE.
Figure 6B:
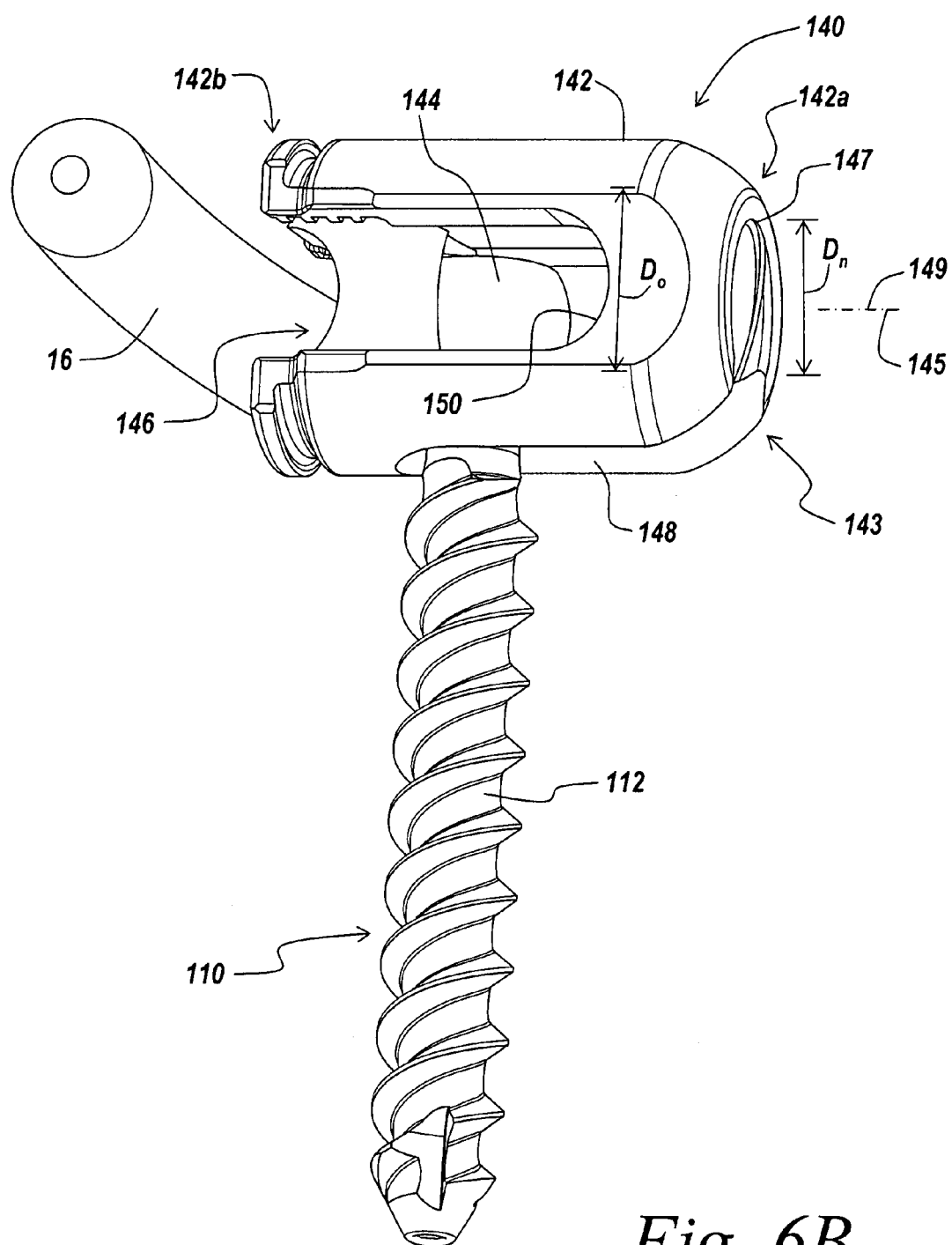
FIG. 6B illustrates the spinal connector of FIG. 6A after rotating to an engagement configuration and sliding with respect to the bone anchor.

FIGS. 6A and 6B illustrate another exemplary embodiment of the spanning connector 140. The spanning connector 140 has a first connecting mechanism 143 to couple the spanning connector 140 to a bone anchor 110, and a second connecting mechanism 144 to couple the spanning connector 140 to the previously inserted spinal fixation element 16. The spanning connector 140 also includes a connector body 142 for coupling the first connecting mechanism 143 with the second connecting mechanism 144.

According to aspects of an exemplary embodiment, the connector body 142 may include an access channel 146 extending through the connector body 142 from a first end 142a of the connector body 142 to a second end 142b of the connector body 142. The access channel 146 is parallel to a central axis 145 of the connector body 142. The access channel 146 allows tool access to the bone anchor head 114 when the connector body 142 is in an insertion configuration with the central axis 145 of the connector body 142 parallel to the shaft 112 of the bone anchor 110. A first diameter $D_o$ of the access channel 146 is sized for insertion of the bone anchor 110 therethrough.

The first connecting mechanism 143 may include a channel neck 147 disposed at the first end 142a of the connecting body 142. A channel diameter narrows from a first diameter $D_o$ to a smaller diameter $D_N$ at the channel neck 147. The smaller diameter $D_N$ at the channel neck 147 is larger than an outer diameter of the bone anchor shaft 112 and smaller than an outer diameter of the bone anchor head 114. The channel neck 147 rotatably couples the connector body 142 to the bone anchor head 114. The first connecting mechanism 143 may also include a side slot 148 extending from the channel neck 147 along the connector body 142 parallel to the central axis 145, the side slot 148 extending through one wall of the connector body 142. A width WS of the side slot 148 is larger than the outer diameter of the bone anchor shaft 112 and smaller than the outer diameter of the bone anchor head 114.

The channel neck 147 and the side slot 148 form a rotatable and sliding coupling for rotating the connector body 142 relative to the bone anchor 110 and for displacing the connector body 142 along the central axis 145 of the central body with respect to the bone anchor 110. The rotatable and sliding coupling allows the connector body 142 to rotate from the insertion configuration, depicted in FIG. 6A, to an engagement configuration with the central axis 145 of the connector body 142 perpendicular to the bone anchor shaft 112. When the connector body 142 is in the engagement configuration, the rotatable and sliding coupling allows the connector body 142 to be displaced relative to the bone anchor 110 along the central axis 145 of the connector body 142 which is also the axis of engagement 149.

Figure 6C:
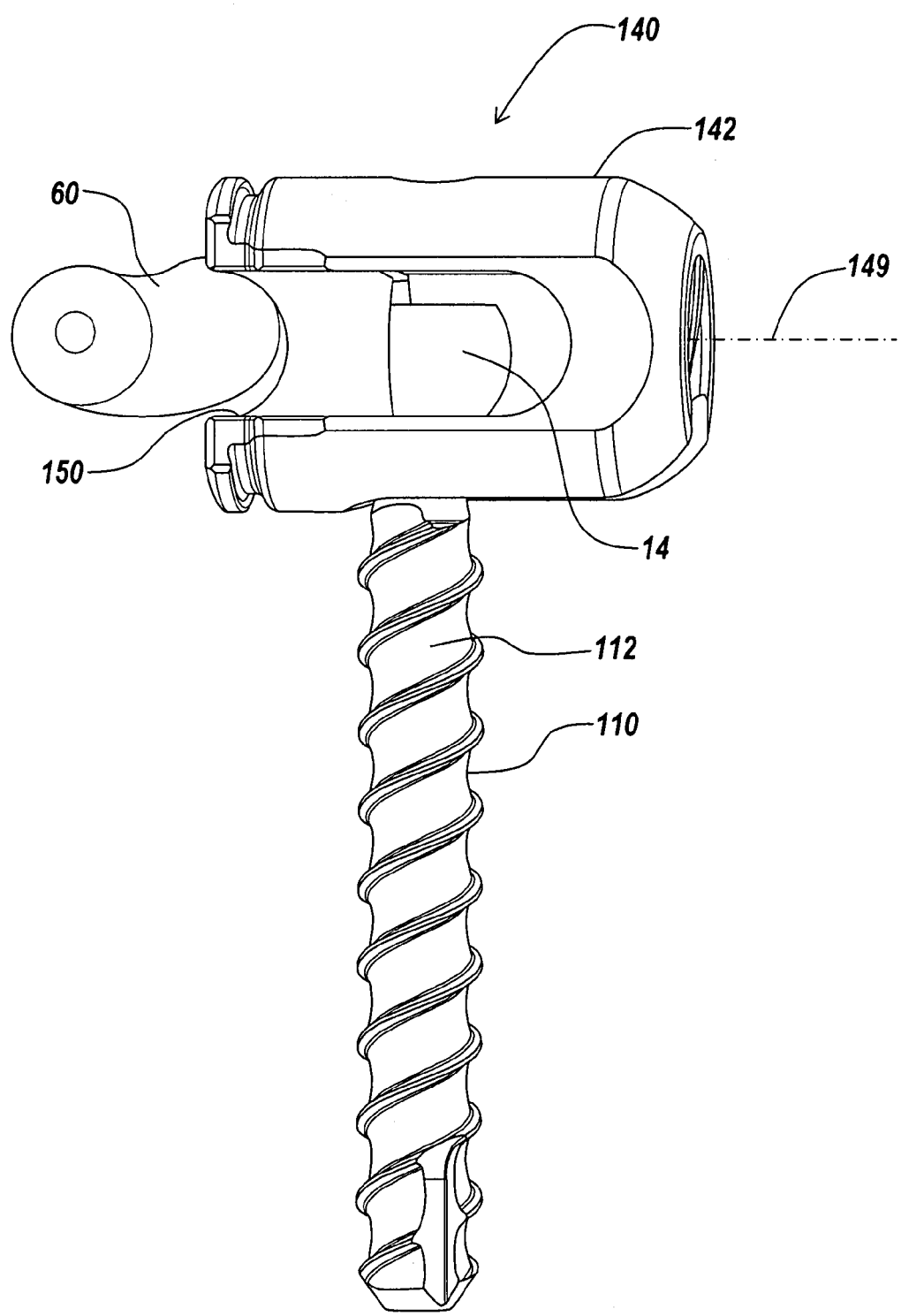
FIG. 6C illustrates the spanning connector of FIG. 6A engaging the SFE.
Figure 6D:
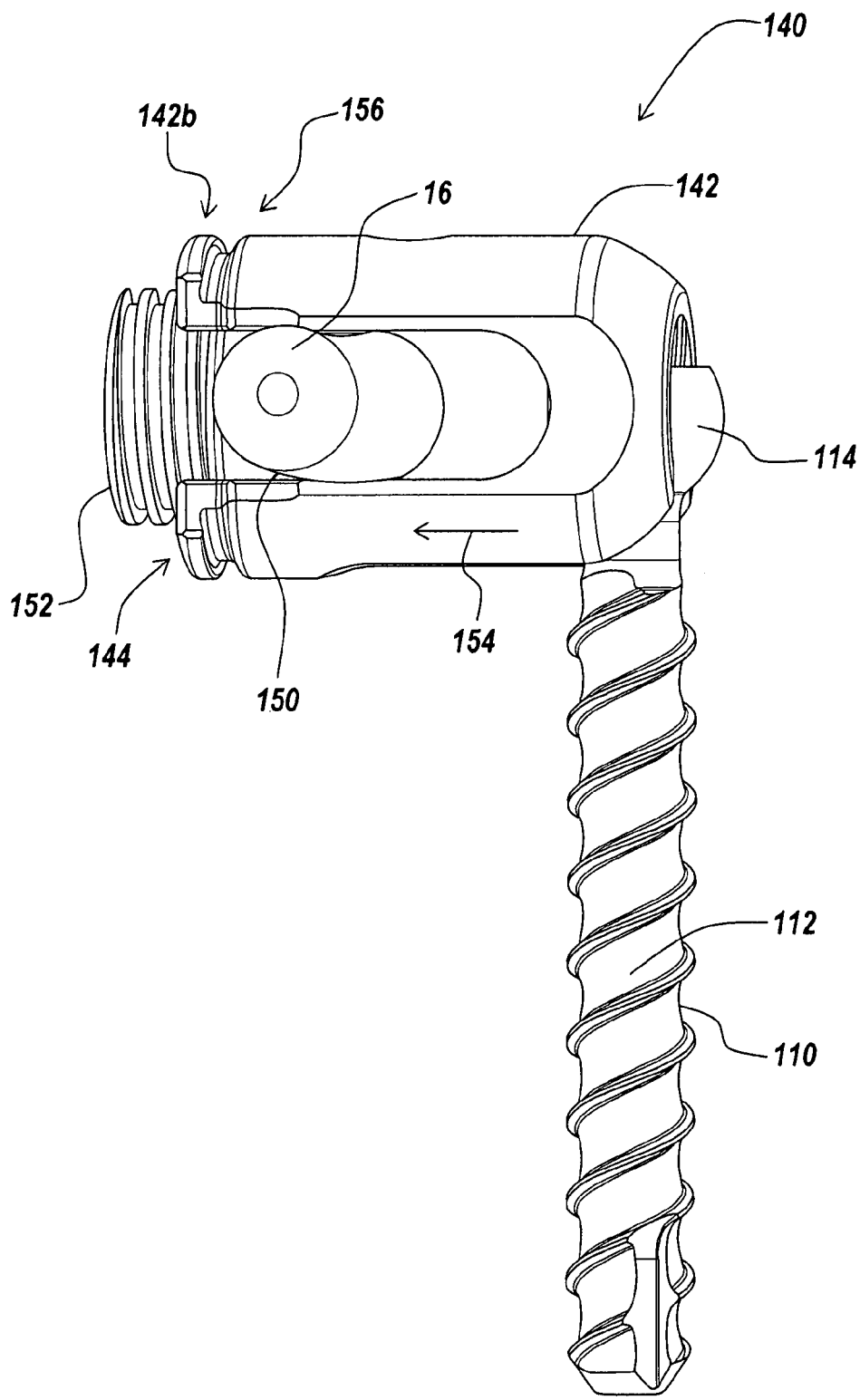
FIG. 6D illustrates the spanning connector of FIG. 6A after receiving the SFE and during insertion of an end lock.

According to aspects of an exemplary embodiment, the spanning connector 140 may include a main slot 150 configured to receive the SFE 16. The main slot 150 extends from the second end 142b of the connector body 142 parallel to the central axis 145 of the connector body 142 and rotated 90 degrees from the orientation of the side slot 148. Engagement of the SFE 16 is depicted in FIGS. 6B, 6C and 6D. In FIG. 6B, the connector body 142 has been rotated to the engagement configuration and displaced along a central axis 149 of the connector body 142 away from the SFE 16. The connector body 142 may be rotated and displaced simultaneously to provide sufficient space between the second end 142b of the connector body 142 and the SFE 16 to complete the rotation. In FIG. 6C, the connector body 142 is being displaced along the engagement axis 149 toward the SFE 16 and is about to receive the SFE 16 in the main slot 150. In FIG. 6D, the connector body 142 has been maximally displaced along the engagement axis 149 toward the SFE 16 and the SFE 16 has been received in the main slot 150. The second connecting mechanism 144 may also include an end lock 152 configured to engage threads 151 in the second end 142b of the connector body 142 blocking the main slot 150 and securing the SFE 16 in the connector body 142.

In addition to connecting the SFE 16 to the offset bone anchor 110, an exemplary embodiment of the spanning connector 140 can decrease a separation distance between the SFE 16 and the bone anchor 110, often referred to as approximating the bone anchor 110 toward the SFE 16. As the end lock 152 is advanced into the connector body 142 of the spanning connector 140, the bone anchor 110 is pulled by the connector body 142 toward the SFE 16 as indicated by arrow 154 in FIG. 6D. Thus, the end lock 152 and the connector body 142 form an approximating mechanism 156.

Figure 6E:
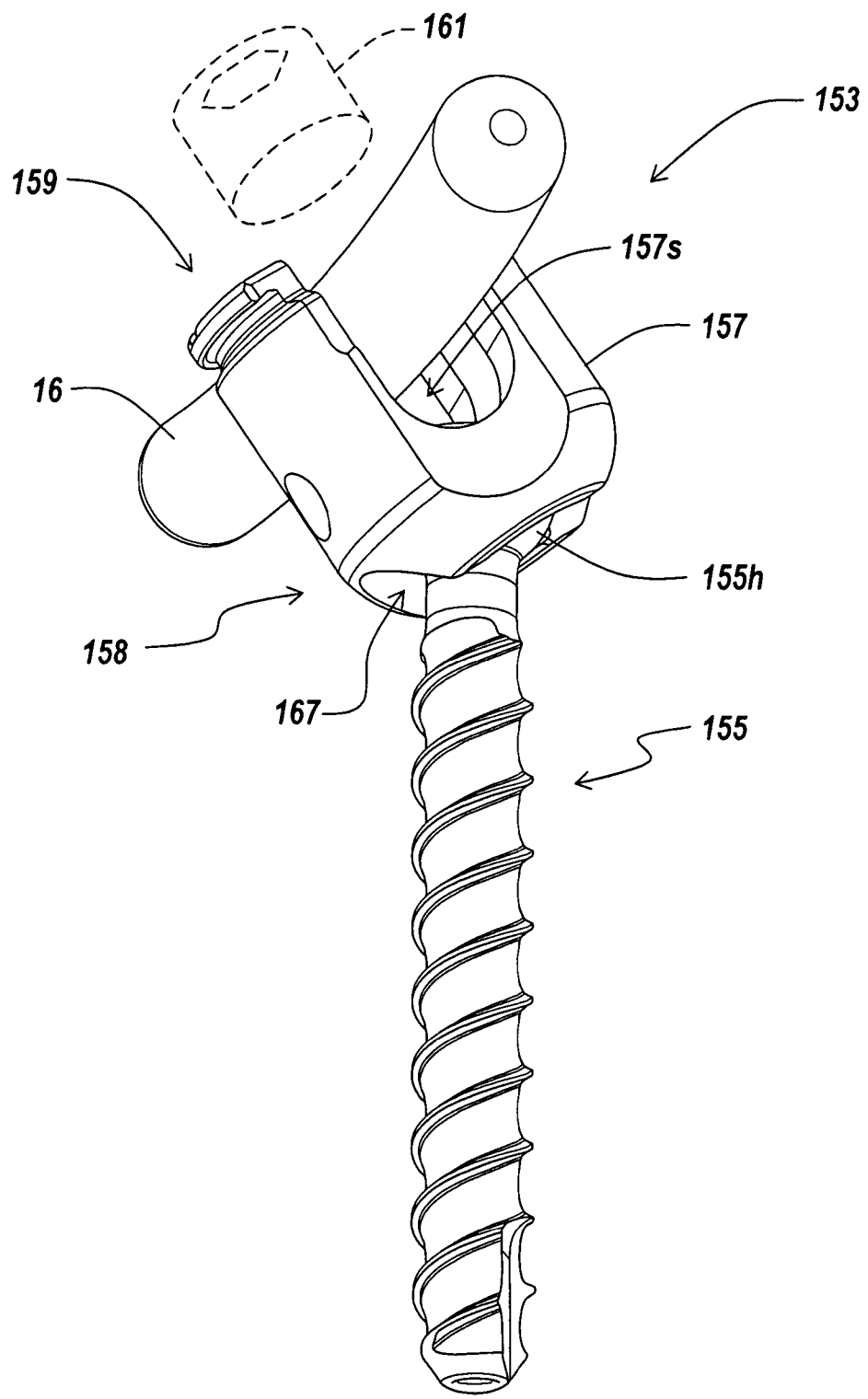
FIG. 6E illustrates another embodiment of a spanning connector that rotates to engage an SFE.

FIG. 6E illustrates another exemplary embodiment of a spanning connector 153 that connects and SFE to an offset bone anchor 155 where the spanning connector 153 rotates from an insertion configuration to an engagement configuration to receive the SFE 16, but a connector body 157 of the spanning connector 153 does not slide toward the SFE 16. A first connecting mechanism 158 couples the connector body 157 and a head of the bone anchor 155h. A rotation slot 167 in the connector body 157 allows the connector body 157 to rotate relative to the bone anchor head 155h. A set screw 161 and a main slot 157s of the connector body form a second connecting mechanism 159 that couples the connector body 157 and the SFE 16.

Figure 7:
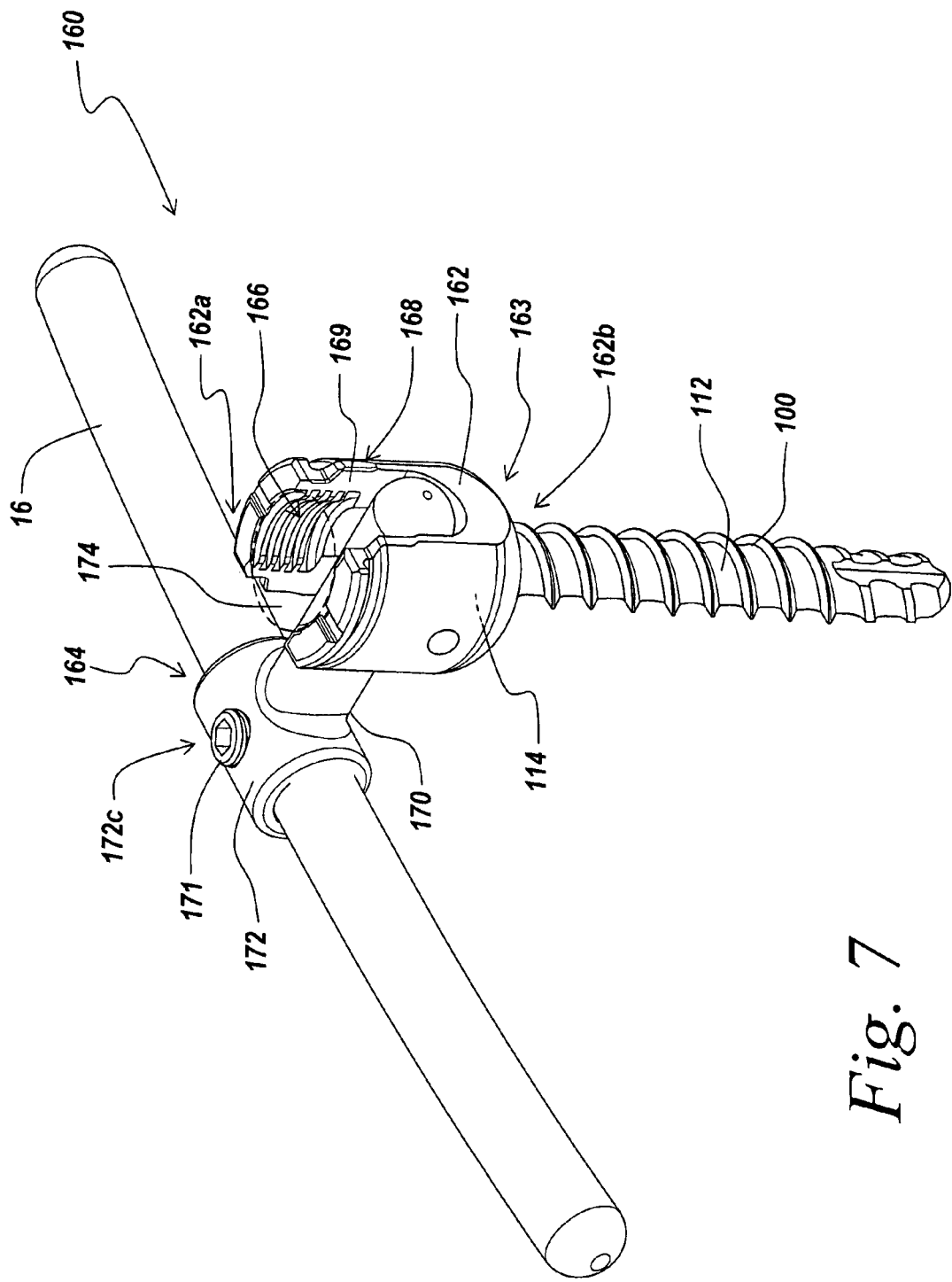
FIG. 7 illustrates an exemplary embodiment of a spanning connector that includes a collar coupled to the SFE.

FIG. 7 illustrates another exemplary embodiment of the spanning connector 160 that connects the SFE 16 to an offset bone anchor 110, such as pedicle screw. The spanning connector 160 has a first connecting mechanism 163 to couple the spanning connector 160 to a bone anchor 110, and a second connecting mechanism 164 to couple the spanning connector 160 to the previously inserted spinal fixation element 16. The spanning connector 160 also includes a connector body 162 for coupling the first connecting mechanism 163 with the second connecting mechanism 164.

According to aspects of an exemplary embodiment, the connector body 162 includes a channel 166 extending from a proximal end 162a of the connector body 162 to a distal end 162b of the connector body 162. The channel 166 is configured for insertion of the bone anchor 110 and tool access. The connector body also includes a receiver 168 for receiving an extender 170. The receiver 168 may include a slot 169 in the connector body 162 as depicted in FIG. 7. The first connecting mechanism 163 may couple the connector body 162 with the bone anchor head 114. The connector body 162 may be able to pivot in multiple directions relative to the bone anchor head 114. An example of a suitable connector body 162 that may pivot in multiple directions with respect to an anchor head 114 is a canulated polyaxial screw used with the VIPER system produced by DePuy Spine, Inc. of Raynham, Mass., and described in U.S. Pat. No. 7,179,261.

The second connecting mechanism 164 may include a collar 172 slidably coupled with the SFE 16. The collar 172 may include a threaded channel 172c for receiving a set screw 171. The set screw 171 may be used to lock a position of the collar 172 with respect to the spinal fixation element 16. The extender 170 may be coupled with the sliding collar 172 and configured to be engaged by the receiver 168. The second connecting mechanism 164 may also include a securing element 174 configured to engage threads on an interior surface of the channel 166 and to apply force to press the extender 170 against the connector body 162 securely coupling the extender 170 and the connector body 162. The securing element 174 may also lock a position of the connector body 122 with respect to a bone anchor head 114.

The SFE 16 may be inserted with the sliding collar 172 and the extender 170 already coupled with the SFE 16. After the bone anchor 110 is inserted, the extender 170 may be coupled to the connector body 162. Alternatively, the sliding collar 172 may be inserted with the SFE 16 and the extender 170 may be inserted after insertion of the bone anchor 100, and then attached connector body 162. The extender 170 may then be coupled with the sliding collar 172 and secured to the connector body 162.

Figure 8A:
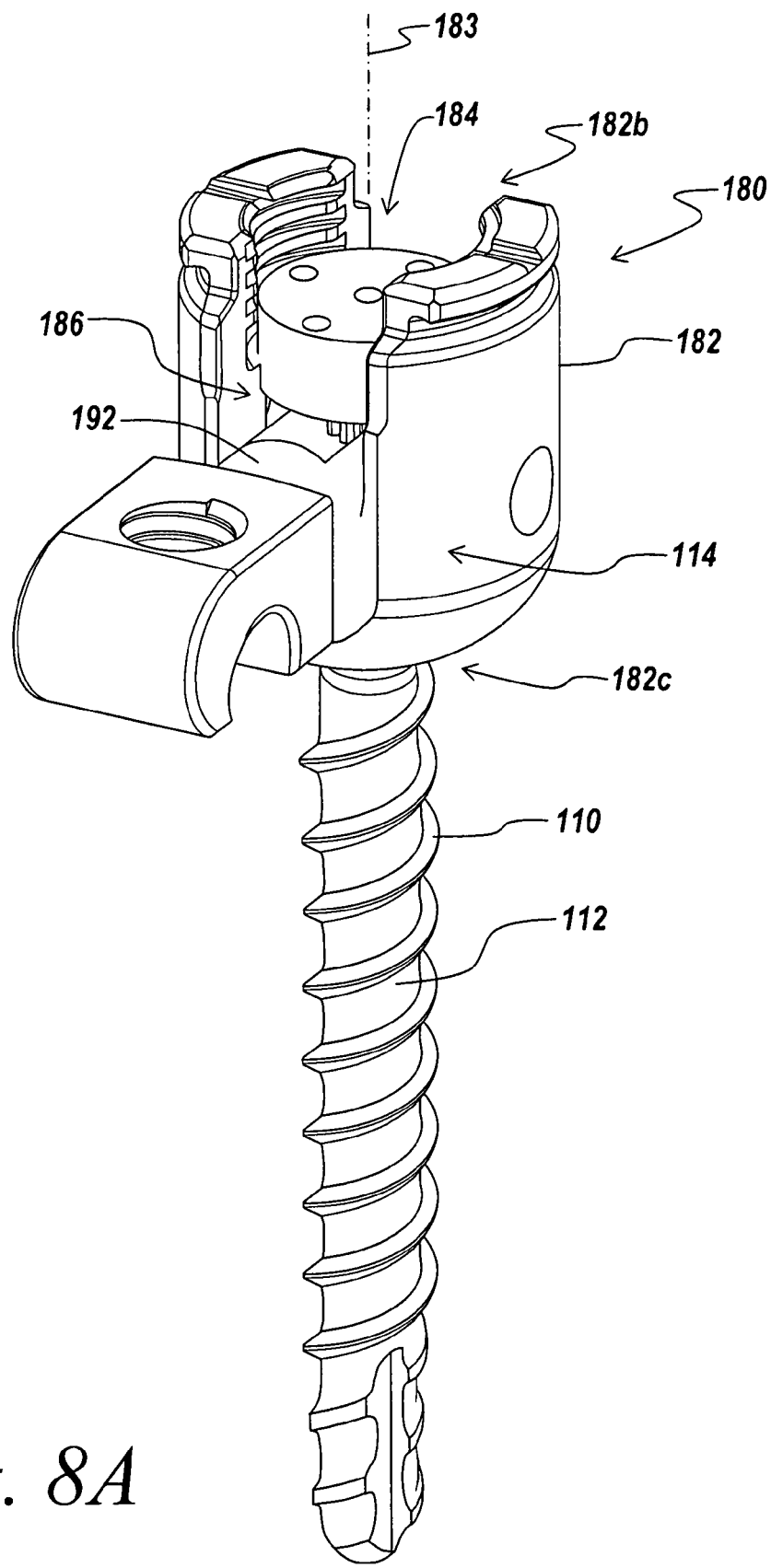
FIG. 8A illustrates a spanning connector including a gear drive, according to aspects of an exemplary embodiment.

FIG. 8A illustrates another exemplary embodiment of the spanning connector 180 that connects the SFE 16 to an offset bone anchor 110 and that can decrease the separation distance between the SFE 16 and the bone anchor 110. The spanning connector 180 may have a gear drive 186 that is configured to extend and retract a connector arm 192 for engaging the SFE 16 and approximating the bone anchor 110. The spanning connector 180 has a first connecting mechanism to couple the spanning connector 180 to a bone anchor 110, and a second connecting mechanism to couple the spanning connector 180 to the previously inserted spinal fixation element 116. The spanning connector 180 also includes a connector body 182 for coupling the first connecting mechanism with the second connecting mechanism.

According to aspect of the exemplary embodiment, the spanning connector 180 may include a body channel 184 extending from a distal end 182a of the connector body 182 to a proximal end 182b of the connector body 182. The body channel 184 extends along a central axis 183 of the connector body 182. The body channel 184 allows insertion of the bone anchor 110 and tool access to the bone anchor head 114. At a distal end 182a the connector body 182 may couple with the bone anchor head 114.

According to other aspects of an exemplary embodiment, the second connecting mechanism may include a gear drive 186 disposed in the body channel 184. Elements of the gear drive 186 are depicted in the exploded view of the spanning connector 180 illustrated in FIG. 8B and in the cross-sectional exploded view of the spanning connector 180 illustrated in FIG. 8C. The gear drive 186 includes a controlling element 187 having a top side 187t and a bottom side 187b. A pinion gear 188 is disposed on the bottom side 187b of the controlling element 187. The top side 187t of the controlling element 187 has an instrument coupling to allow an instrument to engage the controlling element 187. In this case the instrument coupling is a plurality of recesses 189a-189e configured to engage an instrument. The controlling element 187 is configured to rotate about the central axis 183 of the connector body 182. The gear drive 186 also includes the connector arm 192 that extends from the connector body 182. The connector arm 192 has a rack gear 193 configured to engage the pinion gear 188 of the controlling element 187. The rack gear 193 may be disposed in a channel 194 of the connector arm 192. The rack gear 193 and the pinion gear 188 form a rack and pinion system that converts rotational motion of the controlling element 187 into linear extension and retraction of the connector arm 192. The gear drive 186 and the connector arm 192 form an approximation mechanism 198 for reducing the distance between the SFE 16 and the bone anchor 110.

The second connecting mechanism may also include an SFE engager 195 disposed at an end of the connector arm 192 for engaging the SFE 16. The SFE engager may include a elongate recess 196 for receiving the SFE 16 and a locking element 197 for securing the SFE 16 in the elongate recess 196. The connector arm 192 may be extended to engage the SFE 16 by receiving it in the elongate recess 196. Once the SFE 16 is engaged, retraction of the connector arm 192 decreases the distance between the SFE 16 and the bone anchor 110, also known as approximation of the bone anchor.

Another exemplary embodiment of a spanning connector is a clamp-type spanning connector 220 that connects a SFE 17 to an offset bone anchor 210 depicted in FIGS. 9A and 9B. FIG. 9A depicts a side view of the spanning connector 220 and FIG. 9B depicts a side cross-sectional view of the spanning connector 220. The spanning connector 220 includes a connector body 222 with a top side 222t, a bottom side 222b, and a channel 222c for passing a shaft 212 of the bone anchor 210 therethrough. The channel 222c forms a first connecting mechanism 242 that connects the bone anchor 210 and the spanning connector 220. The connector body 222 also includes a recess 224 formed on the bottom side 222b of the connector body. The recess 224 is configured to contact a surface of the SFE 17 clamping the SFE 17 against a seat element 213 of the bone anchor 210, forming the second connecting mechanism 243. The spanning connector 220 may also include a securing element 230 that exerts force on the top side 222t of the connector body 222 to secure the connector body 222 against the SFE 17. The top side 222t of the connector body 222 may be slanted so that that a first force exerted by the securing element 230 on the connector body 222 in the direction of arrow 251 when the securing element is tightened 230 causes a second force on the connector body 222 in the direction 252. The channel 222c in the connector body 222 may be sufficiently wide to allow the connector body 222 to move in the direction 252 in response to the second force. The motion of the connector body 222 can decrease a separation distance between the SFE 17 and the bone anchor 210, thus forming an approximation mechanism. The spanning connector 220 may be configured to rotate between an insertion configuration and a clamping configuration.

Use of an exemplary embodiment of a spanning connector will be described with reference to the spanning connector 140, because the spanning connector 140 incorporates many different features of exemplary embodiments including rotation of the connector body 142 between an insertion configuration and an engagement configuration, displacement of the connector body 142 with respect to the bone anchor 110, and an approximation mechanism 156. Although the spanning connector 140 is useful to illustrate many features of exemplary embodiments, it is only a representative of a particular exemplary embodiment and does not incorporate all features of all exemplary embodiments. In use, the spanning connector 140 depicted in FIGS. 6A through 6D is inserted into a patient vertebra through a minimally invasive surgical access port after the SFE 16 has been inserted and positioned in the patient. The bone anchor 110 is inserted into and coupled with the connector body 142 before the bone anchor 110 and the connector body 142, which are coupled in an insertion configuration, are inserted into the patient vertebra. The bone anchor 110 and connector body 142, in the insertion configuration depicted in FIG. 6A, are inserted into the patient vertebra through a minimally invasive surgical access port such as a cannula. The bone anchor 110 is inserted to a depth where the bone anchor head 114 is at the same height as the SFE 16.

The connector body 142 is both rotated and displaced along the central axis 145 of the connector body 142 away from the SFE 16. As previously noted, the connector body 142 may be rotated and displaced simultaneously to provide sufficient space between the second end 142b of the connector body 142 and the SFE 16 to complete the rotation. Once the connector body 142 is in an engagement configuration as depicted in FIG. 6B, the connector body 142 is moved toward the SFE 16 along the engagement axis 149 until the SFE 16 is received in the main slot 150 of the connector body 142. Once the SFE 16 is within the main slot 150 an end lock 152 may be positioned at the second end of the connector body 142 and screwed into place coupling the SFE 16 with the connector body 142.

Advancing the end lock 152 further toward the first end 142a of the connector body 142 exerts a force on the SFE 16 in the direction of the bone anchor head 114 and exerts an opposing force on the bone anchor head 114 through the connector body 142 in the direction of the SFE 16, as depicted in FIG. 6D. Further advancing the end lock 152 reduces the distance separating the bone anchor 110 and the SFE 16.

Figure 10A:
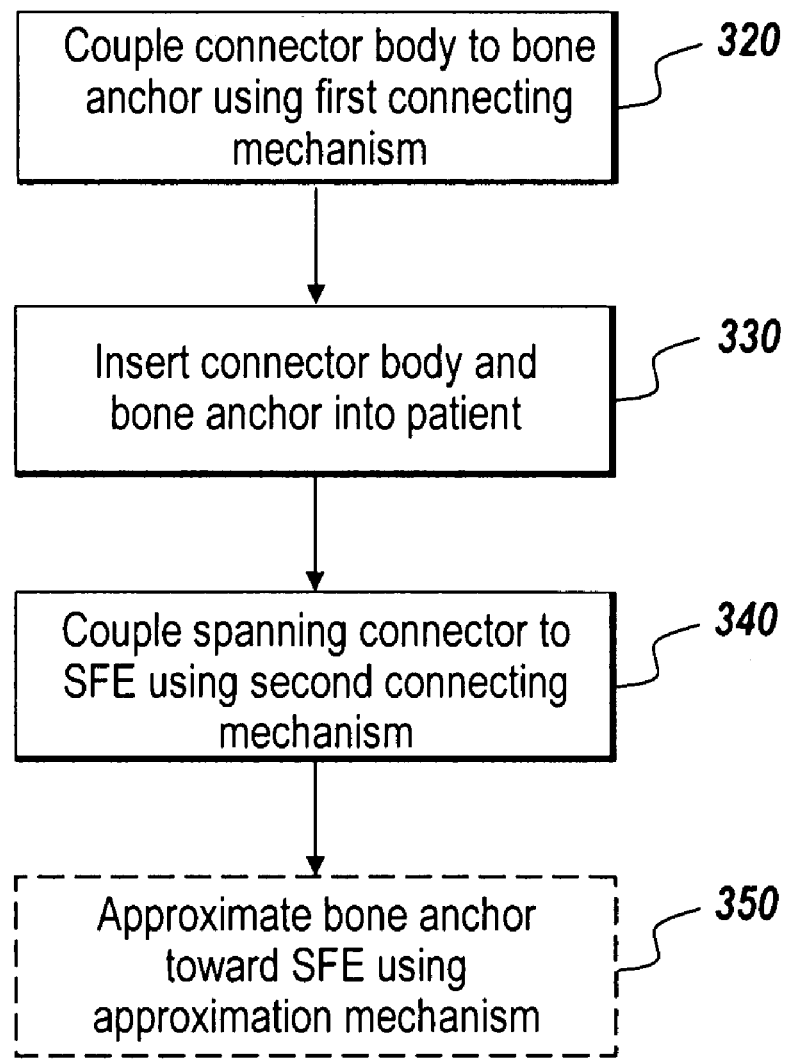
FIG. 10A is a flow diagram of an exemplary embodiment of a method for connecting the offset bone anchor to the previously inserted spinal fixation element using a spanning connector.

FIG. 10A illustrates an exemplary embodiment of a method 300 for connecting an offset bone anchor to a previously inserted spinal fixation element using a spanning connector. Solely for illustrative purposes, the method will primarily be described with reference to the spanning connector 140 depicted in FIGS. 6A through 6D. A spanning connector 140 may be provided. The connector body 142 is coupled to the bone anchor, such as the bone anchor 110 using a first connecting mechanism (step 320). The connector body 142 and the bone anchor (bone anchor 110) are inserted into a patient, (step) 230. The connector body 142 and the bone anchor may be inserted into the patient through a minimally invasive surgical access port.

As depicted in FIG. 6, the connector body 142 is coupled to the bone anchor, and then the coupled connector body 142 and bone anchor are inserted into the patient. In other embodiments of the method, the bone anchor may be inserted into the patient before the connector body 142 is coupled with the bone anchor. Then the connector body 142 is inserted into the patient and coupled with the bone anchor.

After the bone anchor 110 and connector body 142 are coupled to each other and inserted into the body, the spanning connector 140 is coupled to the previously inserted spinal fixation element 16 using the second connecting mechanism 144 (step 340) coupling the bone anchor with the SFE 16. In other embodiments of the method, the bone anchor may be inserted into the patient, then the spanning connector 142 may be coupled to the SFE 16, and then the connector body 142 may be coupled to the bone anchor. According to aspects of an exemplary embodiment, the method may include using one or more locking elements to secure the connector body 142 to the bone anchor and/or to secure the SFE 16 to the spanning connector 140.

Figure 8B:
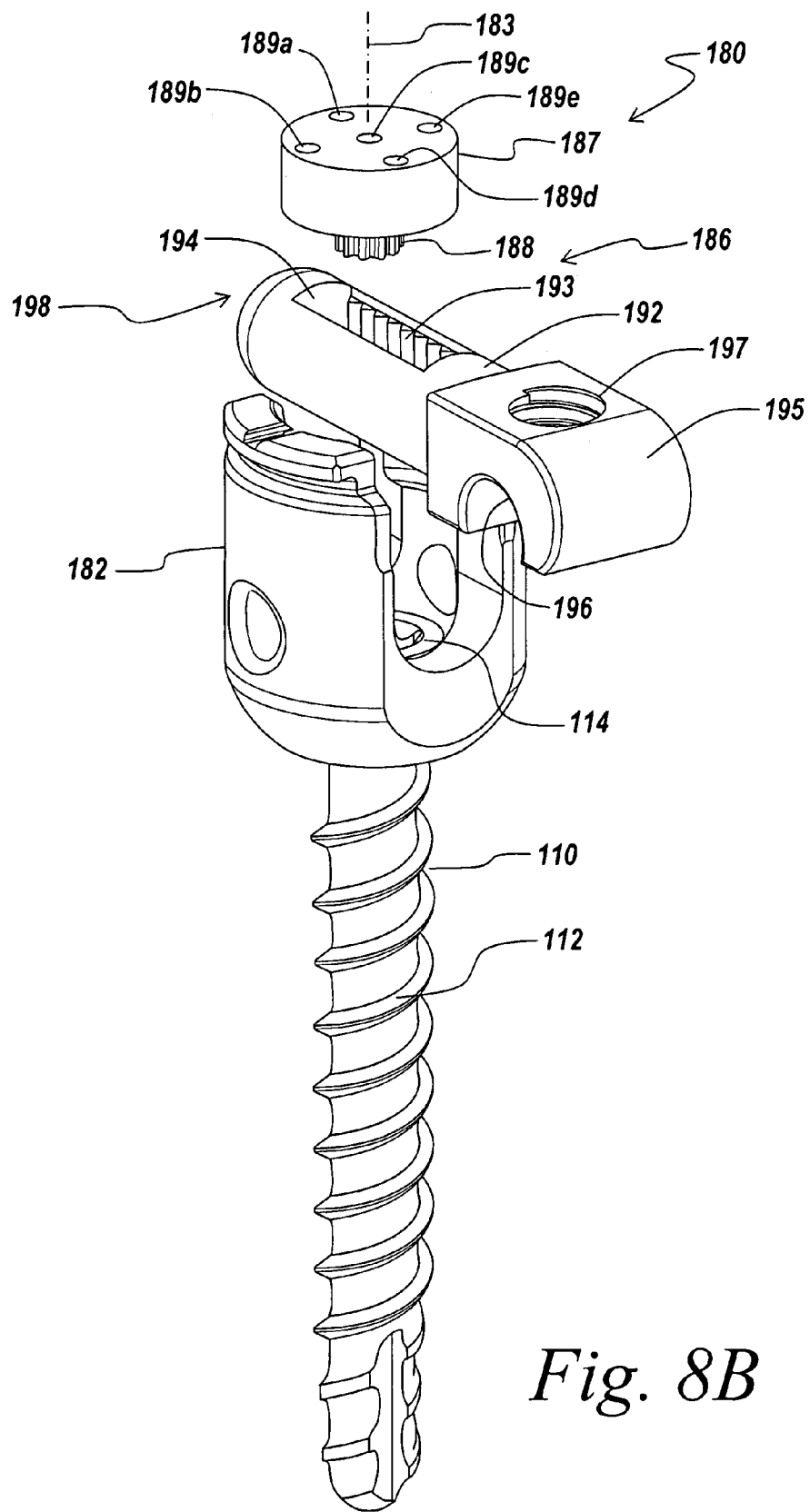
FIG. 8B illustrates an exploded view of the spanning connection depicted in FIG. 8A.
Figure 8C:
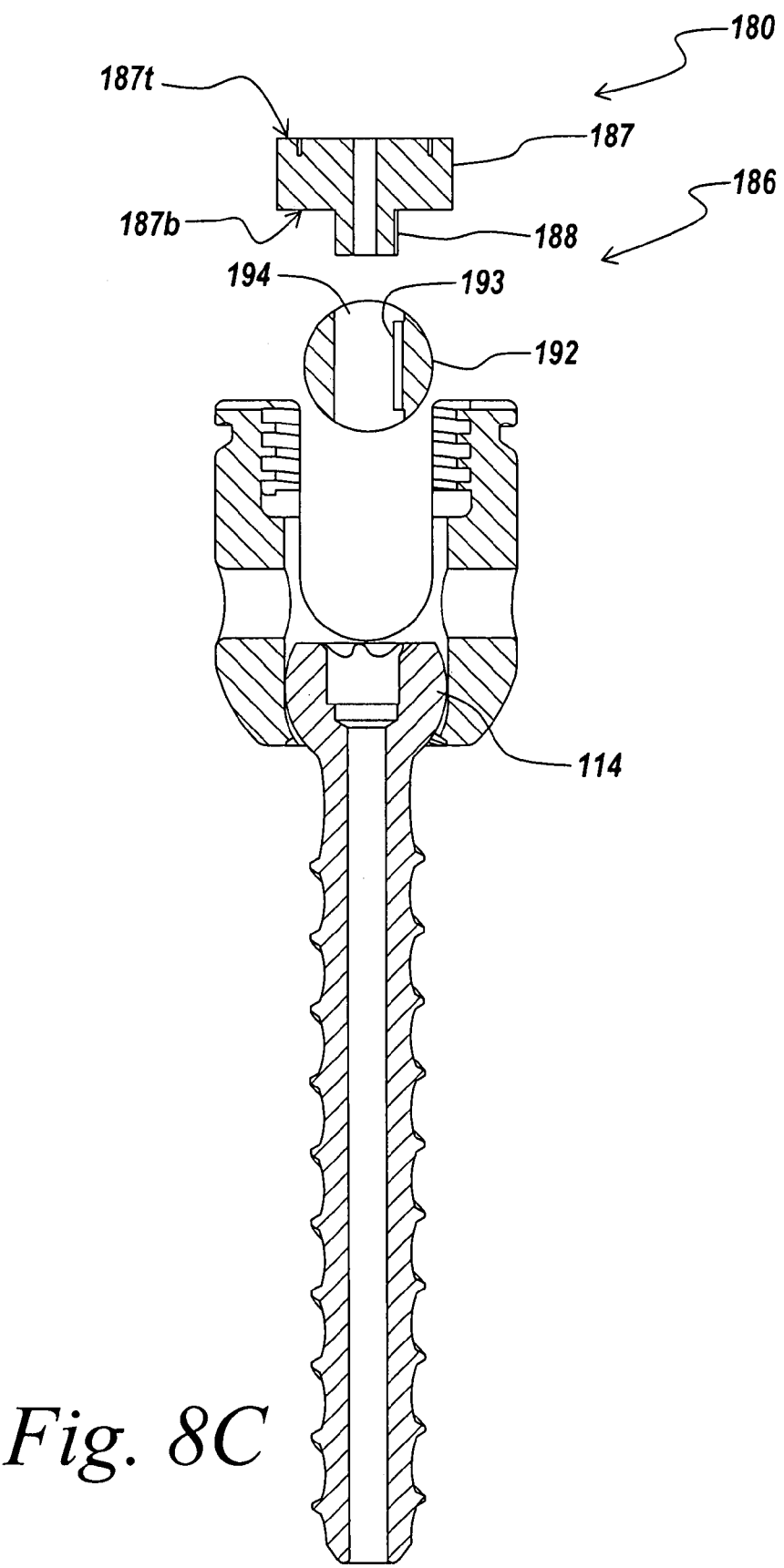
FIG. 8C illustrates a cross-sectional exploded view of the spanning connector depicted in FIG. 8A.

According to other aspects of an exemplary embodiment, the method may include approximating the bone anchor 110 toward the spinal fixation element 16 using an approximating mechanism 156 (step 350), as depicted in FIG. 6D. The approximating mechanism 156 includes the end lock 152 and the connector body 142. Tightening the end lock 152 exerts force on the bone anchor 110 in the direction of arrow 154 to reduce a distance between the bone anchor 110 and the spinal fixation element 15. Another approximating mechanism 198, including a gear drive 186 and a connector arm 192, is depicted in FIGS. 8A through 8C.

Figure 10B:
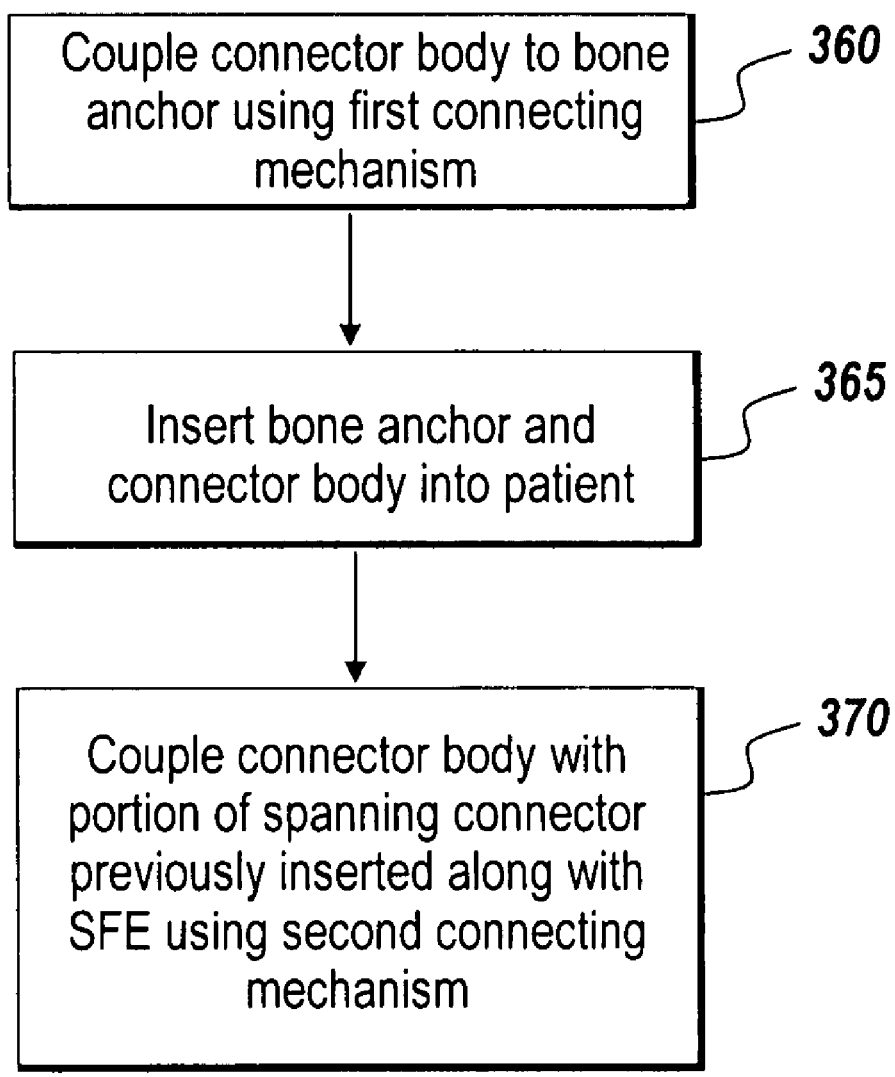
FIG. 10B is a flow diagram of an exemplary embodiment of a method for connecting the offset bone anchor to the previously inserted spinal fixation element where a portion of a spanning connector is previously inserted with the spinal fixation element.

FIG. 10B illustrates another exemplary embodiment of a method 355 for connecting an offset bone anchor 100 to a previously inserted spinal fixation element 16 using a spanning connector 160. Solely for illustrative purposes, the method will primarily be described with reference to the spanning connector 160 depicted in FIG. 7. The connector body 162 is coupled to the bone anchor 100 using the first connecting mechanism 163 (step 360). The bone anchor 110 and the connector body 162 are inserted into a patient (step 365). A portion of the spanning connector, the collar 172 and the extender 170, may have been previously inserted with the SFE 16. The connector body 162 is coupled with the portion of the spanning connector (the collar 172 and the extender 170) using the second connecting mechanism 164 (step 370).

Figure 10C:
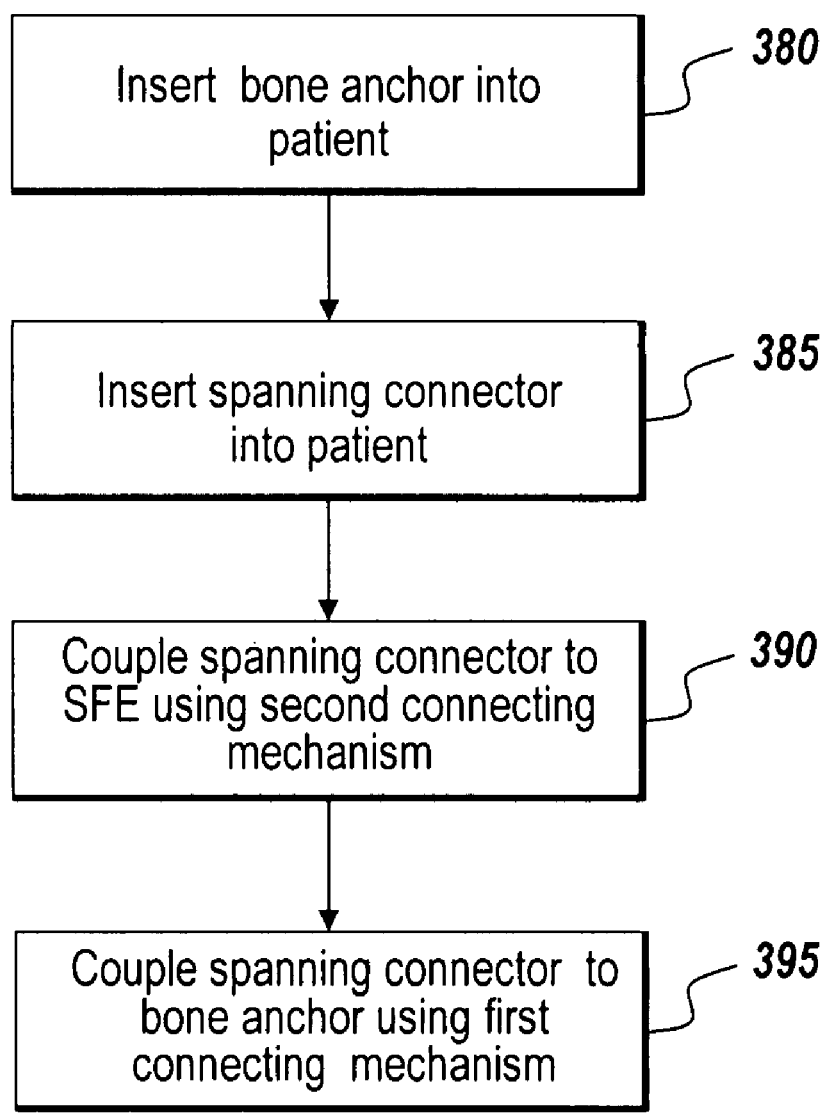
FIG. 10C is a flow diagram of an exemplary embodiment of a method for connecting the offset bone anchor to the previously inserted spinal fixation element using a spanning connector where the spinal anchor is inserted before the spanning connector.

FIG. 10C illustrates another exemplary embodiment of a method 375 for connecting an offset bone anchor 10 to a previously inserted spinal fixation element 16 using a spanning connector. Solely for illustrative purposes, the method will primarily be described with reference to the spanning connector 80 depicted in FIGS. 4A through 4D. The bone anchor 10 is inserted into the patient (step 380), and then the spanning connector 80 is inserted into the patient (step 385). The spanning connector 80 is coupled with the SFE 16 using the second connecting mechanism 84 (step 90). The spanning connector 80 is then coupled with the bone anchor 10 using the first connecting mechanism 83 (step 395).

While the figures depict exemplary embodiments of a spanning connector coupling an SFE to a bone anchor and methods of use, one of ordinary skill in the art will recognize that exemplary embodiments of a spanning connector may couple with many different types of bone anchors, including but not limited to: bolts, screws, hooks, staples, anchors, etc. Additionally, exemplary embodiments of a spanning connector may couple with many different types of spinal fixation elements, including but not limited to: rods, dynamic rods, cables, vertebral body replacements, interbody fusions devices, plates, PDS (posterior dynamic stabilization) elements, etc. Although exemplary embodiments depicted herein allow side engagement with an SFE and/or engagement from above, embodiments may also allow engagement from below an SFE, diagonal engagement and various other engagement orientations.

One skilled in the art will appreciate further features and advantages of the invention based on the above-described embodiments. Accordingly, the invention is not to be limited by what has been particularly shown and described, except as indicated by the appended claims.

While the devices and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. A spanning connector for connecting a spinal fixation element to an offset bone anchor, the spanning connector comprising:
   a first connecting mechanism for coupling the spanning connector to the bone anchor, wherein the spanning connector is directly coupled with a head of the bore anchor;

a second connecting mechanism for coupling the spanning connector to a previously inserted spinal fixation element; and a connector body for coupling the first connecting mechanism with the second connecting mechanism, wherein the connector body is rotatable between an insertion configuration where a central axis of the connector body is substantially parallel to a shaft of the bone anchor and an engagement configuration where the central axis is substantially perpendicular to the shaft of the bone anchor, wherein the connector body comprises an access channel extending through the connector body and parallel to the central axis of the connector body, the access channel for allowing tool access to the head of the bone anchor when the connector body is in the insertion configuration;

wherein the first connecting mechanism comprises a rotatable coupling disposed at a first end of the connector body for rotatably coupling the first end of the connector body to the head of the bone anchor, the rotatable coupling configured to permit the connector body to rotate between the insertion configuration and the engagement configuration;

wherein the second connection mechanism comprises an engaging elongate recess formed on a surface of the connector body, which faces the shaft of the bone anchor, to engage the spinal fixation element in the engagement configuration; and wherein the engaging elongate recess is configured to engage the spinal fixation element from above when the connector body is rotated from the insertion configuration to the engagement configuration.

2. The spanning connector of claim 1, wherein the spanning connector is configured for use in a rod-first spinal surgical technique.

3. The spanning connector of claim 1, the connector body further comprising:

a screw lock for locking a position of the connector body relative to the bone anchor; and a spinal fixation element lock for locking the spinal fixation element in the engaging elongate recess of the connector body, wherein a single set screw controls the screw lock and the spinal fixation element lock.

* * * * *